United States Patent
Pellegrino et al.

(10) Patent No.: US 8,289,387 B2
(45) Date of Patent: Oct. 16, 2012

(54) VISION SYSTEM, METHOD FOR INSTALLING A VISION SYSTEM AND METHOD FOR MANUFACTURING A VISION SYSTEM

(75) Inventors: Luigi Pellegrino, Nardo (IT); Kurt Vonmetz, Bologna (IT); Stefano Santi, Bologna (IT); Fabrizio Guastadini, Bologna (IT)

(73) Assignee: Datalogic Automation S.R.L., Lippo di Calderara di Reno (BO) (IT)

( * ) Notice: Subject to any disclaimer, the term of this patent is extended or adjusted under 35 U.S.C. 154(b) by 499 days.

(21) Appl. No.: 12/666,183

(22) PCT Filed: Jul. 10, 2007

(86) PCT No.: PCT/IB2007/001928
§ 371 (c)(1),
(2), (4) Date: Dec. 22, 2009

(87) PCT Pub. No.: WO2009/007772
PCT Pub. Date: Jan. 15, 2009

(65) Prior Publication Data
US 2010/0201804 A1    Aug. 12, 2010

(51) Int. Cl.
*H04N 7/18* (2006.01)
*G01B 15/02* (2006.01)
(52) U.S. Cl. .......... 348/92; 348/E7.085; 378/70; 378/90
(58) Field of Classification Search .............. 348/92, 348/E7.085; 378/70, 90
See application file for complete search history.

(56) References Cited

U.S. PATENT DOCUMENTS

| | | | |
|---|---|---|---|
| 4,900,907 A | 2/1990 | Matusima et al. | |
| 5,319,182 A | 6/1994 | Havens et al. | |
| 6,066,857 A | 5/2000 | Fantone et al. | |
| 6,160,925 A | 12/2000 | Seo | |
| 6,454,167 B1 | 9/2002 | Barkan et al. | |
| 7,486,773 B2 * | 2/2009 | Maltz et al. | 378/90 |
| 2006/0175411 A1 | 8/2006 | Itou | |
| 2008/0067386 A1 * | 3/2008 | Maltz et al. | 250/311 |
| 2010/0231522 A1 * | 9/2010 | Li | 345/169 |

FOREIGN PATENT DOCUMENTS

| | | |
|---|---|---|
| DE | 125989 | 6/1977 |
| EP | 0133367 A2 | 2/1985 |
| EP | 0426921 A2 | 5/1991 |
| GB | 2310749 A | 9/1997 |

OTHER PUBLICATIONS

International Search Report from corresponding PCT Application No. PCT/IB2007/001928 dated Feb. 18, 2008.

* cited by examiner

*Primary Examiner* — Khanh Dinh
(74) *Attorney, Agent, or Firm* — Duane Morris LLP

(57) ABSTRACT

A fixed vision system includes a sensor having a sensitive surface for acquiring an image of an object on a detecting plane, and a light-emitting device for generating a luminous reference figure on the detecting plane including an emission surface, and an objective through which a luminous radiation (from the object to the sensor) and a further luminous radiation (from the light-emitting device to the object) pass. The sensor and the light-emitting device are positioned such that, when the detecting plane is focused by the objective on the sensor, the sensitive surface is on the image plane generated by the objective or on a respective mirror plane with respect to the image plane and the emission surface of the light-emitting device is on the image plane or on a respective mirror plane with respect to the image plane.

50 Claims, 22 Drawing Sheets

VISION SYSTEM, METHOD FOR INSTALLING A VISION SYSTEM AND METHOD FOR MANUFACTURING A VISION SYSTEM

FIELD OF THE INVENTION

The invention relates to a vision system, in particular a fixed vision system for acquiring images, a method for installing a vision system and a method for manufacturing a vision system.

BACKGROUND OF THE INVENTION

Hereinafter in this description and in the subsequent claims the expression "vision system" indicates an apparatus that is able to acquire and possibly process images that is used in various applications such as, for example, automatic inspection for quality control, measurements without contact, selecting and positioning industrial pieces, reading and checking optical information, inspecting materials for detecting defects or dimensional checks, supervision, biometric recognition and access control, etc.

Hereinafter in this description and in the subsequent claims, the expression "optical information" indicates a graphic representation having the function of storing encoded or non-encoded information. A particular example of optical information consists of linear or two-dimensional optical codes, in which the information is coded through suitable combinations of elements with a preset shape, for example, square, rectangular, or hexagonal, with a dark colour (normally black) separated by light elements (spaces, normally white), such as barcodes, stacked codes and the bidimensional codes in general, colour codes, etc. The term "optical information" further comprises, more in general, also other graphic forms, including particular printed characters (letters, numbers, etc) and shapes ("patterns") (such as, for example, stamps, logos, signatures, digital fingerprints etc). The term "optical information" comprises graphic representations that are detectable across the entire wavelength comprised between infrared and ultraviolet and therefore not only in the visible light field.

An example of a vision system that is able to acquire images associated with an object placed on a supporting plane (for example distance, volume, overall dimensions of the object, or data identifying the object, in particular an optical code associated with the object) by acquiring and processing an acquisition zone at the supporting plane.

The vision system is a system—in particular a fixed system—capable of capturing images of objects or people, of subjects in general, and in particular of optical information, by means of a plurality of possible acquisition techniques.

For example, acquisition can be performed by illuminating a subject, collecting with a suitable optical receiving system, for example comprising an objective, the light diffused by the subject on a sensor consisting of an array of light-sensitive elements of a linear or matrix type, for example of the CCD or CMOS type, and generating an image signal by means of an electronic system integrated or associated with the sensor. The image signal, generated in analogue or digital form, can then be processed in the same apparatus or in a separate image processing system.

Typically, in vision systems dedicated to the acquisition of images containing coded optical information, such as barcodes, the image signal in digital form is decoded to extract the information content of the code.

Apparatuses of this type are known as linear or matrix TV cameras or cameras, and when they read optical information, they are also known as code-reading devices of the "imager" type.

Hereinafter in this description and in the subsequent claims, the expression "fixed vision system" indicates a vision system the position of which with respect to the supporting plane is not varied during operation, for example a vision system for use without human operation ("unattended system"), in particular at a conveyor belt (or other moving means) on which objects to be detected are moved, but also at a station in which an operator inserts the objects to be detected manually. Detecting the objects may comprise reading an optical code and/or measuring a distance and/or a volume, etc.

A drawback of known vision systems is that they are rather complicated to install, in particular, dedicated operations are necessary to check and, possibly, to adjust the focussing thereof. In known vision systems fixed-focus and adjustable-focus systems are distinguished.

A further drawback of known vision systems is that an installer is unable to define visually when the system is focussed. Checking focussing, in fact, requires the vision systems—i.e. the detecting sensors with which the vision systems are provided—to be switched on to detect the image of a sample figure. If the detected image is not clear, it is necessary for the installer to intervene manually on the objective to adjust the focussing of the vision systems.

This checking method, comprising a plurality of consecutive refinements of focussing, involves the acquisition of a series of sample images, so actuation thereof takes a long time.

In addition, it necessary to provide a display, for example the monitor of a computer, to enable the installer to examine the detected images. In other words, installation of the known vision systems requires the provision of complex and expensive equipment.

SUMMARY OF THE INVENTION

An object of the invention is to improve known vision systems, in particular fixed vision systems.

Another object is to obtain a fixed vision system the focussing of which is easily checkable and adjustable during installation.

A further object is to simplify installation of known vision systems, in particular of fixed vision systems.

A still further object is to obtain a method for installing a fixed vision system that enables the focussing of the vision system to be easily checked and adjusted during installation.

A still further object is to obtain a method for manufacturing a fixed vision system the focussing of which is easily checkable and adjustable during installation.

A further object is to provide an indication of the positioning of a vision system with respect to a detecting plane.

In a first aspect of the invention, a fixed vision system is provided comprising a sensor for acquiring an image of an object on a detecting plane, said sensor comprising a sensitive surface, a light-emitting device for generating a luminous reference figure on said detecting plane, said light-emitting device comprising an emission surface, at least an objective through which a luminous radiation and a further luminous radiation pass, said luminous radiation coming from said object and being directed to said sensor and said further luminous radiation coming from said light-emitting device and being directed to said object, characterised in that said sensor and said light-emitting device are positioned in such a way that, when said detecting plane is focussed by said objective on said sensor, said sensitive surface of said sensor is on the image plane generated by said objective or on a respective mirror plane with respect to said image plane and said emission surface of said light-emitting device is on said image plane or on a respective mirror plane with respect to said image plane.

The image plane is the plane on which the objective generates the image of an object.

The mirror plane of an image plane is a further image plane generated by interposing a reflecting optical element between the objective and the image plane. The reflecting optical element may be, for example, a mirror, a semitransparent mirror, a dichroic mirror.

Owing to this aspect of the invention, it is possible to obtain a vision system the focussing of which is easily checkable and adjustable during installation.

In fact, as the luminous radiation coming from the object and directed to the sensor and the further luminous radiation coming from the light-emitting device and directed to the object pass through the same objective, and as the sensitive surface of the sensor is on the image plane generated by the objective or on a respective mirror plane with respect to the image plane and the emission surface of the light-emitting device is on the image plane or on a respective mirror plane with respect to the image plane, a focussing condition of the detecting plane on the sensor corresponds to a focussing condition of the luminous reference figure on the detecting plane.

The focussing condition of the luminous reference figure on the detecting plane may be checked visually—i.e. with the naked eye—by an installer, without it being necessary to activate the sensor and display sample images by means of a dedicated display.

Some of the known vision systems are provided with an aiming device, comprising, for example, one or more sources of light, that generates on the detecting plane an aiming figure that indicates an area framed by the sensor, i.e. the field of view [FoV]) of the sensor. In certain cases, the aiming figure may provide an indication that enables the installer to position correctly a vision system with respect to a detecting plane.

The aiming device is in no way able to provide an indication of focussing of the vision system as the length of an optical path defined between the aiming device and the object to be detected is different from the length of an optical path defined between the object and the sensor. This is because in some known vision systems the sources of light of the aiming device are fixed to a front face of the sensor package and project away from the latter. In addition, in these known vision systems, the sensitive zone of the sensor is housed in a cavity of the package and is recessed with respect to the aforesaid front face.

In known vision systems when the sensitive surface of the sensor is positioned on the image plane generated by the objective the emission surface of the aiming device is not positioned on the image plane or on a respective mirror plane with respect to the image plane, as said sources of light are arranged in an extremely approximate manner with respect to the sensor.

Further, as the correspondence between the focussing condition of the detecting plane on the sensor and the focussing condition of the reference figure on the detecting plane depends on the fact that the sensitive surface of the sensor is on the image plane generated by the objective or on a respective mirror plane with respect to the image plane and the emission surface of the light-emitting device is on the image plane or on a respective mirror plane with respect to the image plane, but does not depend on the type of objective used, different types of objectives can be associated with the vision system according to the invention. In other words, it is possible to provide a plurality of interchangeable objectives to be associated with the vision system and choose each time the most suitable objective for the type of measurement to be made. In particular, the choice of objective may depend on the distance of the vision system from the detecting plane and/or from the dimensions of the zone to be framed. It is possible, for example, to use normal commercial C-mount objectives.

It is possible to adjust the focussing manually, for example by means of a nut with which the objective is provided.

It is further possible to provide motor-driven adjustment of the focussing by means of suitable controls.

In a second aspect of the invention, a method is provided for installing a fixed vision system, comprising a sensor for acquiring an image of an object on a detecting plane, said sensor comprising a sensitive surface, a light-emitting device for generating a luminous reference figure on said detecting plane, said light-emitting device comprising an emission surface, at least an objective through which a luminous radiation and a further luminous radiation pass, said luminous radiation coming from said object and being directed to said sensor and said further luminous radiation coming from said light-emitting device and being directed to said object, said sensor and said light-emitting device being positioned in such a way that, when said detecting plane is focussed by said objective on said sensor, said sensitive surface of said sensor is on the image plane generated by said objective or on a respective mirror plane with respect to said image plane and said emission surface of said light-emitting device is on said image plane or on a respective mirror plane with respect to said image plane, comprising the steps of:

positioning said vision system at a first distance from said detecting plane, switching on said light-emitting device;

adjusting said objective until said luminous reference figure appears to be visually focussed on said detecting plane.

Owing to this aspect of the invention, it is possible to obtain a method that enables focussing of a vision system during installation to be checked and adjusted.

During installation, an installer visually checks—i.e. with the naked eye, without any need for complex and costly instruments such as a computer display or monitor—the focussing of the luminous reference figure generated by the light-emitting device on the detecting plane. If the luminous reference figure is not focussed on the detecting plane, it is sufficient for the operator to act on the objective, typically by means of a control nut, to perform fine adjustment of the focussing. It is also possible to provide automatic driving of the nut by means of control devices. The method according to the invention enables checking and fine adjustment of the focussing of a vision system to be achieved by switching on only the light-emitting device, i.e. without switching on the sensor being necessary and detecting, through the sensor, images of a sample figure, as occurs in known vision systems.

This is possible as the vision system is shaped in such a way that focussing of the detecting plane on the sensor is ensured when the luminous reference figure appears focussed on the detecting plane to the eye of the installer.

In an embodiment, after the objective has been adjusted so that the luminous reference figure appears to be visually focussed on said detecting plane, said detecting plane is moved in such a way that between said vision system and said detecting plane a second distance is defined. Acting on a diaphragm of said objective is also provided to check the luminosity and the depth of field of said objective until said luminous reference figure appears to be visually focussed on said detecting plane at said second distance.

Subsequently, further moving said detecting plane is provided in such a way that between said vision system and said detecting plane a third distance is defined, said first distance having an intermediate value between the values of said second distance and of said third distance, and checking if said luminous reference figure appears to be visually focussed on said detecting plane at said third distance.

If said luminous reference figure does not appear visually focussed on said detecting plane at said third distance further acting on said diaphragm is provided for further controlling the luminosity and the depth of field of said objective until said luminous reference figure appears visually focussed on said detecting plane at said third distance.

In this way, it is possible to obtain a method that enables objects arranged at different distances from the vision system to be viewed correctly, these distances belonging to a preset range.

It is in fact possible to proceed in the following manner. With the diaphragm of the objective completely open, the focussing of the objective is adjusted using an object that is arranged at a distance corresponding to an intermediate value within the aforesaid range. Subsequently, by using, for example, an object arranged at a shorter distance from the vision system, i.e. a distance having a value near the minimum limit of the aforesaid range, it is checked whether the luminous reference figure appears to be visually focussed on the detecting plane. If this does not occur, the light and the depth of field of the objective are adjusted, keeping the focus fixed. This corresponds to a partial closure of the diaphragm of the objective. Still subsequently, by using an object arranged at a greater distance from the vision system, i.e. a distance having a value near the maximum limit of the aforesaid range, it is checked whether the luminous reference figure appears to be visually focussed on the detecting plane. If this does not occur, it is possible to further adjust the luminosity and the depth of field of the objective until the luminous reference figure appears to be visually focussed on the detecting plane. This corresponds to a further partial closure of the diaphragm of the objective. In particular, in the case of a fixed vision system mounted above a conveying system it is possible to detect correctly images of objects conveyed by the conveying system and which have differing heights from one another. For example, it is possible to view correctly images of packs having a height the value of which belongs to a preset range.

Once the range is known—i.e. the maximum height and the minimum height of the packs to be examined—it is possible, during the installation step, to adjust once and for all the focussing, the luminosity and the depth of field of the objective in such a way that all the packs having a height belonging to the range are viewed correctly.

In a third aspect of the invention, a method is provided for manufacturing a fixed vision system, comprising a sensor for acquiring an image of an object on a detecting plane, said sensor comprising a sensitive surface, a light-emitting device for generating a luminous reference figure on said detecting plane, said light-emitting device comprising an emission surface, at least an objective through which a luminous radiation and a further luminous radiation pass, said luminous radiation coming from said object and being directed to said sensor and said further luminous radiation coming from said light-emitting device and being directed to said object, deflecting means arranged for deviating said luminous radiation and/or said further luminous radiation, comprising the steps of:

positioning said vision system at a preset distance from said detecting plane, activating said sensor to detect a sample image, adjusting said objective until said sample image is viewed focussed by said sensor, switching on said light-emitting device, varying the position of said light-emitting device and/or of said deflecting means until a configuration is reached in which said luminous reference figure appears to be visually focussed on said detecting plane, in said configuration said sensor and said light-emitting device being positioned in such a way that, when said detecting plane is focussed by said objective on said sensor, said sensitive surface of said sensor is on the image plane generated by said objective or on a respective mirror plane with respect to said image plane and said emission surface of said light-emitting device is on said image plane or on a respective mirror plane with respect to said image plane.

In a fourth aspect of the invention, a method is provided for manufacturing a fixed vision system, comprising a sensor for acquiring an image of an object on a detecting plane, said sensor comprising a sensitive surface, a light-emitting device for generating a luminous reference figure on said detecting plane, said light-emitting device comprising an emission surface, at least an objective through which a luminous radiation and a further luminous radiation pass, said luminous radiation coming from said object and being directed to said sensor and said further luminous radiation coming from said light-emitting device and being directed to said object, deflecting means arranged for deviating said luminous radiation and/or said further luminous radiation, comprising the steps of:

positioning said vision system at a preset distance from said detecting plane, switching on said light-emitting device, adjusting said objective until said luminous reference figure appears to be visually focussed on said detecting plane, activating said sensor to detect a sample image, varying the position of said sensor and/or of said deflecting means until a configuration is reached in which said sample image is viewed focussed by said sensor, in said configuration said sensor and said light-emitting device being positioned in such a way that, when said detecting plane is focussed by said objective on said sensor, said sensitive surface of said sensor is on the image plane generated by said objective or on a respective mirror plane with respect to said image plane and said emission surface of said light-emitting device is on said image plane or on a respective mirror plane with respect to said image plane.

Owing to these aspects of the invention, it is possible to manufacturing a vision system the focussing of which is easily checkable and adjustable during installation. The above methods in fact enable a vision system to be manufactured and then be made available to an installer in which the focussing of the detecting plane on the sensor corresponds to a condition of focussing of the reference luminous image on the detecting plane—visually observed by the installer with the naked eye.

This enables the installation of the vision system to be significantly simplified, and in particular checking and adjusting the focussing of the sensor during installation. In these circumstances, in fact, it is not necessary to switch on the sensor to acquire a sample image, but it is sufficient to evaluate the focussing of the luminous reference figure and to act on the objective, if necessary.

Owing to the above methods, a visual evaluation of the degree of focussing of the luminous reference figure on the detecting plane enables an operator entrusted with assembly of the vision system to vary the relative positions of the sensor, of the light-emitting device and of the deflecting means until a configuration is reached in which the sensitive surface of the sensor is on the image plane generated by the objective or on a respective mirror plane with respect to the image plane and the emission surface of the light-emitting device is on the image plane or on a respective mirror plane with respect to the image plane.

The visual evaluation of the degree of focussing of the luminous reference figure on the detecting plane is operationally much easier than a direct experimental measurement of the distance between the sensor and the deflecting means and the distance between the light-emitting device and the deflecting means, this also in consideration of the small dimensions of the latter.

In an embodiment, the sensor and the deflecting means are maintained in a fixed position and the light-emitting device is moved with respect to the deflecting means until a distance defined between the emission surface of the light-emitting device and the deflecting means is the same as a further distance defined between the sensitive surface of the sensor and the deflecting means.

Alternatively, it is possible to keep the sensor and the light-emitting device in a fixed position and move the deflecting means.

Still alternatively, it is possible to keep in a fixed position the sensor and move both the light-emitting device and the deflecting means.

BREIF DESCRIPTION OF THE DRAWINGS

The invention can be better understood and implemented with reference to the attached drawing that show some embodiments thereof by way of non-limiting example, in which.

DETAILED DESCRIPTION

Figure 1:
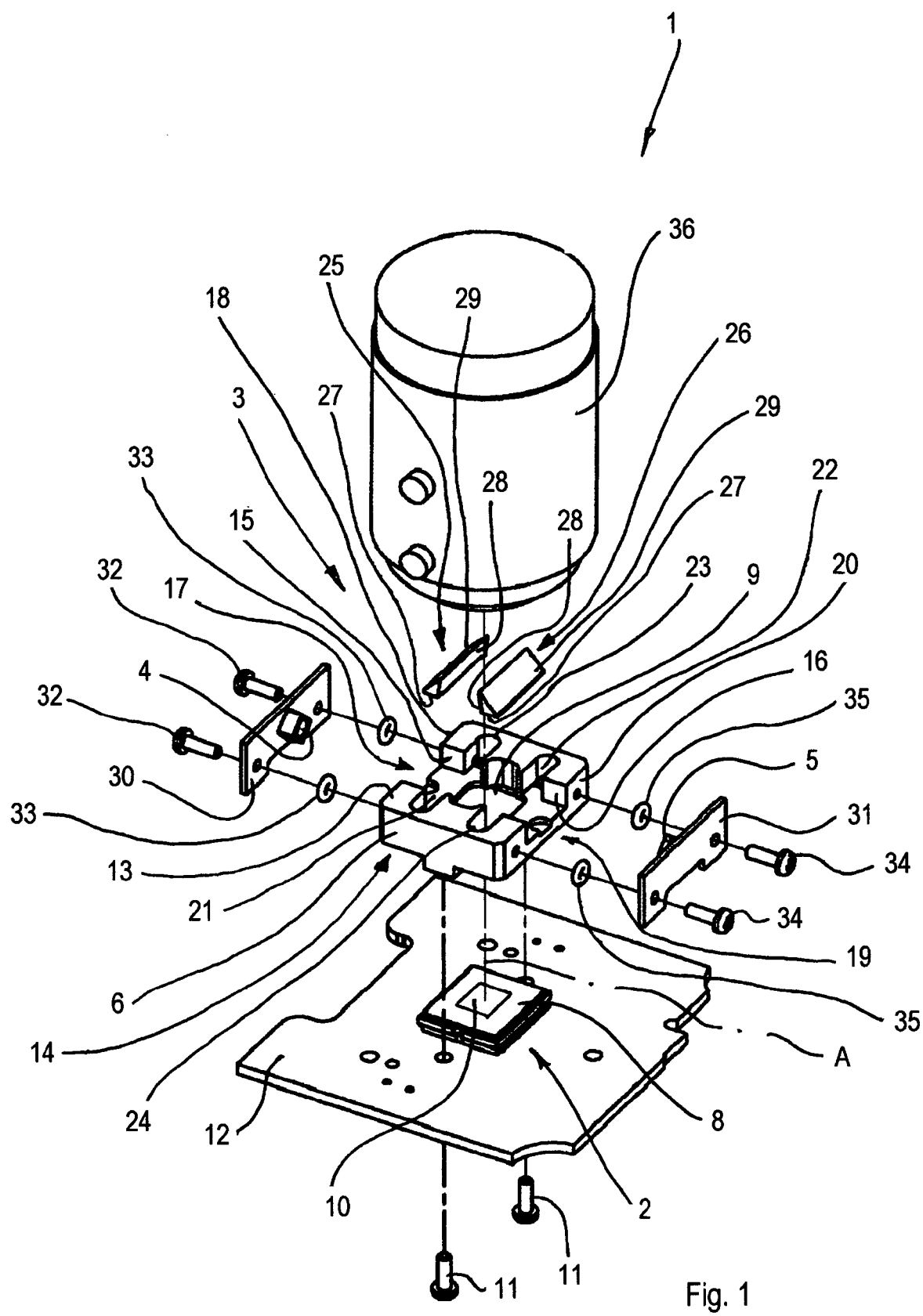
FIG. 1 is an exploded perspective view from above of a vision system.
Figure 2:
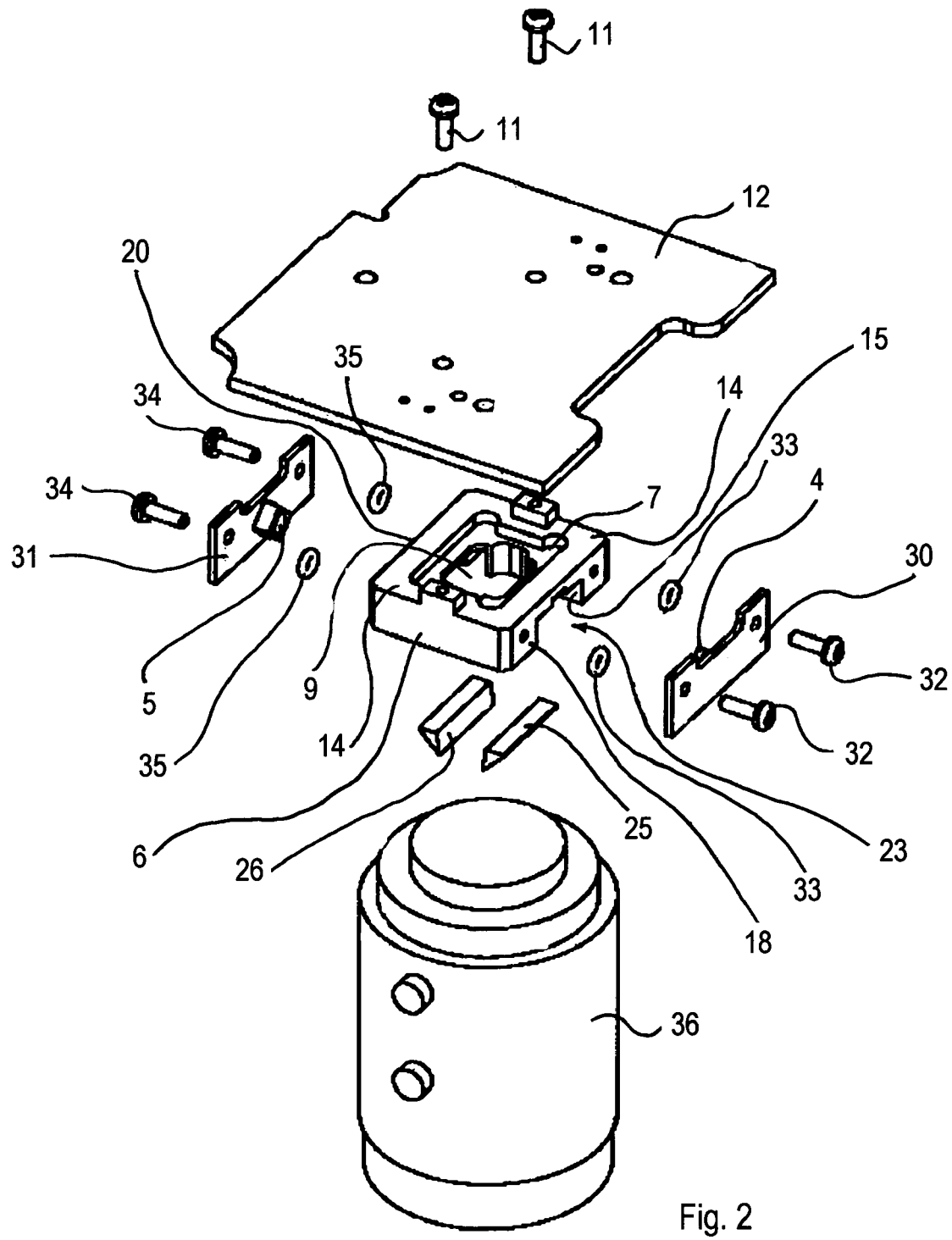
FIG. 2 is an exploded perspective view from below of the vision system in FIG. 1.
Figure 3:
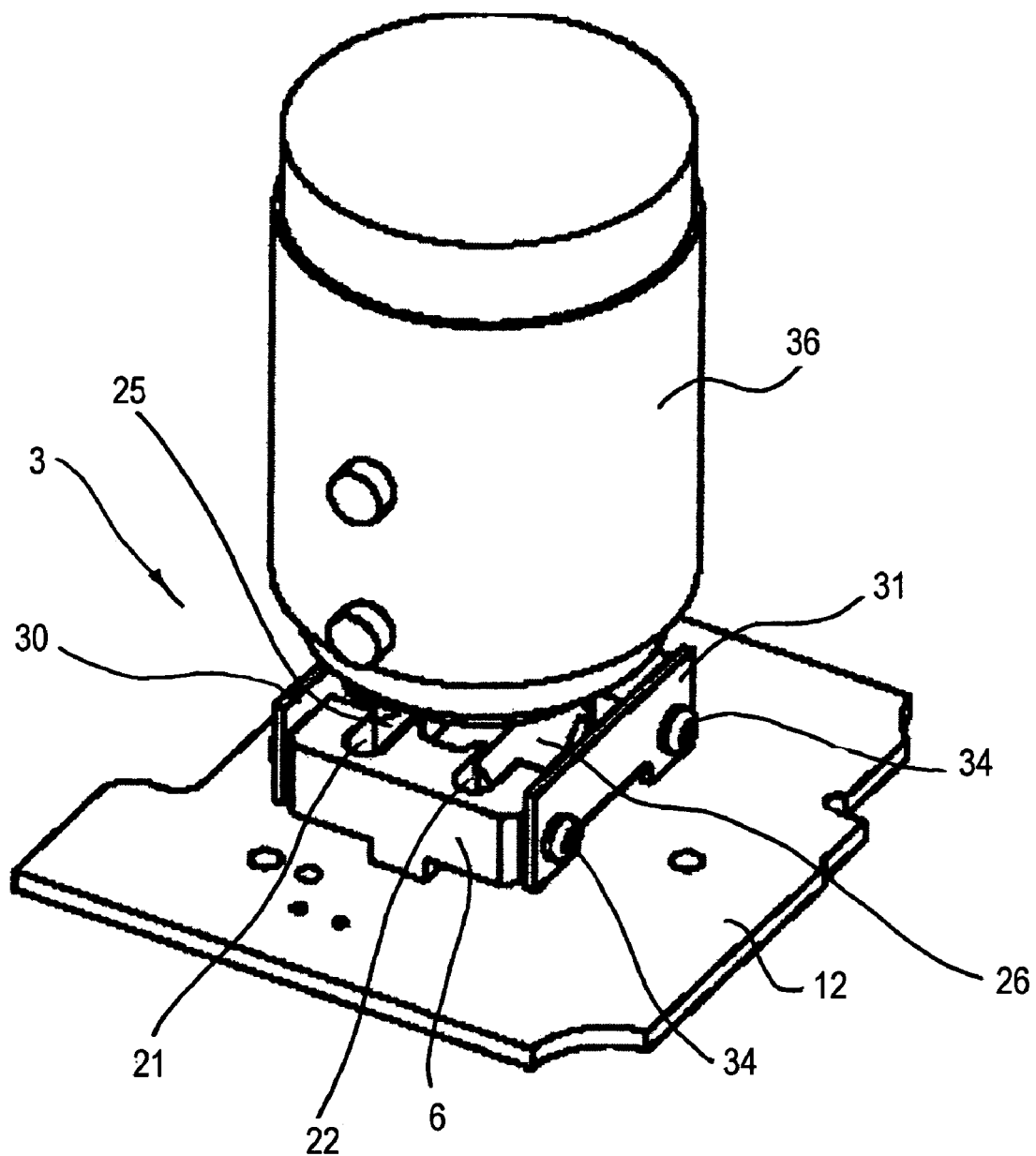
FIG. 3 is an exploded perspective view from above of the vision system in FIG. 1, in an assembled configuration.
Figure 4:
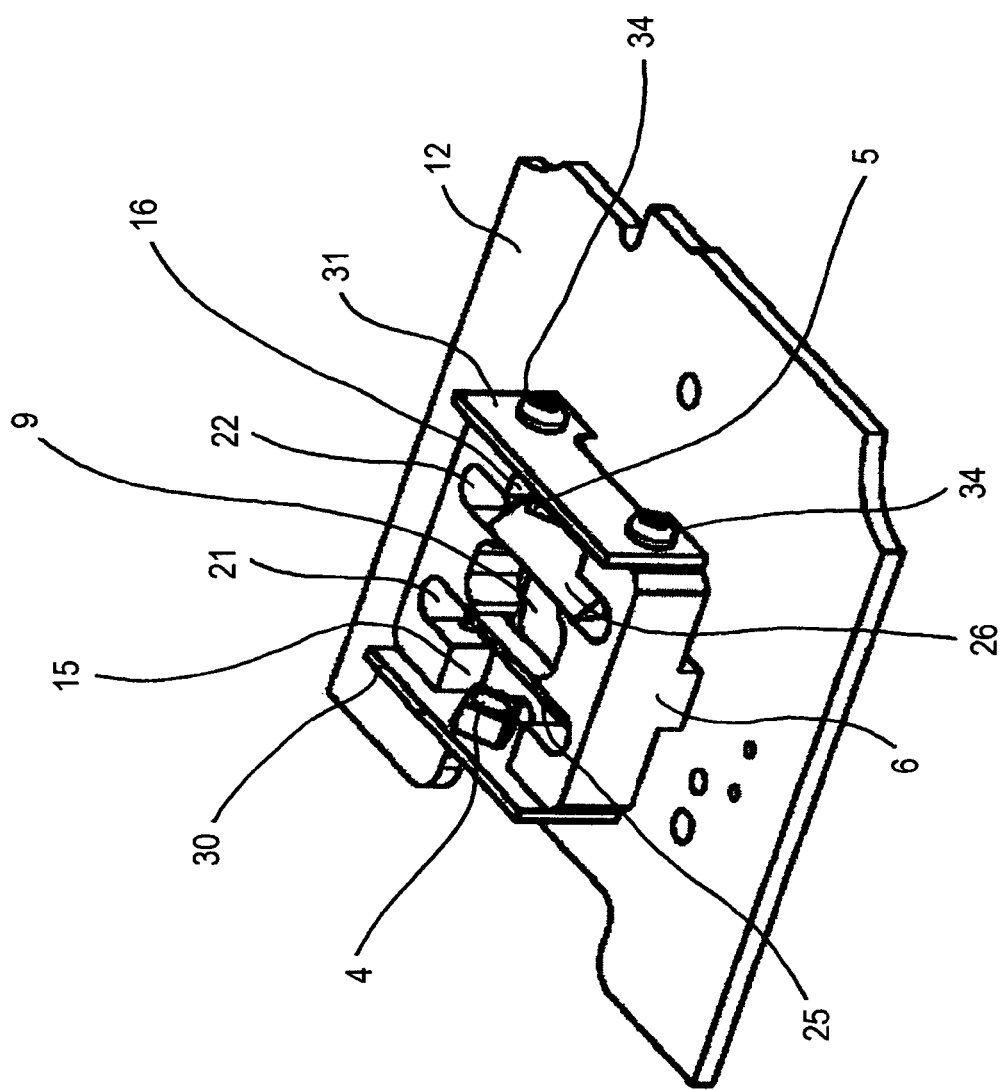
FIG. 4 is a view like that in FIG. 3, in which an objective has been removed from the vision system.

With reference to FIGS. 1 to 5 and 23 to 31 a vision system 1 for acquiring images is shown.

The vision system 1 is installed in a fixed position in such a way as to acquire images of objects arranged on a detecting plane 38. The detecting plane can be associated with a conveying device, for example a conveyor belt that supports and moves the objects.

In an embodiment, the vision system detects optical information, in particular coded optical information, for example a barcode applied to the object. The sensor 2 comprises a two-dimensional array of photosensitive elements, of the type CCD o CMOS. Alternatively, the sensor may be of linear type.

The vision system comprises an illuminating device 80, shown in FIGS. 23 to 30, arranged for illuminating an object and a sensor 2 arranged for receiving the diffused or reflected light from the object to detect an image of the object.

The vision system 1 further comprises a light-emitting device 3 arranged for generating a luminous reference FIG. 39 on the detecting plane 38.

Figure 19:
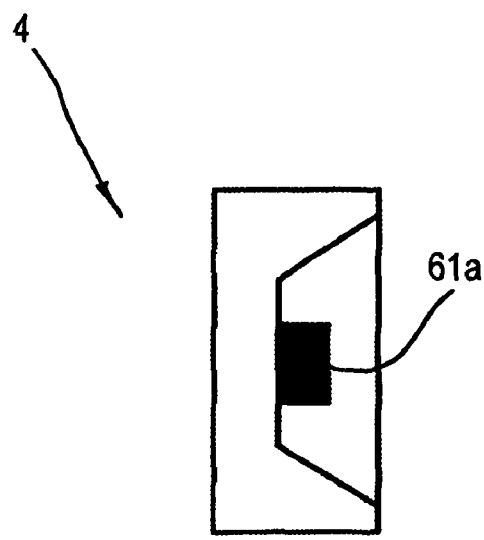
FIG. 19 is a schematic cross section of a LED of a light-emitting device of a vision system.

The light-emitting device 3 comprises a first LED 4 of the SMD type, shown in detail in FIG. 19, comprising an emission surface 61a, and a second LED 5 of the SMD type, comprising an emission surface 61b. Alternatively to the first LED 4 and to the second LED 5 other types of light sources can be provided that will be disclosed in greater detail below. The light-emitting device 3 further comprises a base body 6 having a seat 7 arranged for receiving the package 8 of the sensor 2 in a shapingly coupled manner. Advantageously, the mechanical coupling of the base body 6 with the package 8 of the sensor 2 and with the first LED 4 and the second LED 5 is manufactured in an extremely precise manner with tolerances of even less than a tenth of a millimeter. Such close tolerances permit good repeatability of mounting operations and ensure precision in generating the reference luminous figures with respect to the FoV.

The base body 6 further comprises a through hole 9 that surrounds a sensitive surface 10 of the sensor 2 when the package 8 of the sensor 2 is positioned inside the seat 7. In other words, the through hole 9 enables a beam of light coming from the object to reach the sensitive surface 10.

The base body 6 is intended to be connected, for example via screws 11, to a plate 12 to which the sensor 2 is fixed. The plate 12 is for example a common printed circuit. The plate 12 is in turn fixed to an external enclosure 56 of the vision system 1, shown in FIGS. 15 and 16 and in FIGS. 23 to 31, so as to ensure perfect alignment of all the components with respect to the external enclosure 56.

The base body 6 comprises a first face 13 intended to face the object and a second face 14, opposite the first face 13, intended to face the sensor 2 and from which the seat 7 leads away.

The through hole 9 extends between the first face 13 and the second face 14, which are substantially parallel to one another.

The through hole 9 has a longitudinal axis substantially coinciding with an optical axis A of the sensor 2. The aforesaid longitudinal axis is substantially perpendicular to the first face 13 and to the second face 14.

The base body 6 further comprises a first gap 15 that receives the first LED 4 and a second gap 16 that receives the second LED 5.

The first gap 15 comprises a first opening 17 obtained in a side face 18 of the base body 6.

The second gap 16 comprises a second opening 19 obtained in a further side face 20, opposite the side face 18, of the base body 6.

The side face 18 and the further side face 20 are arranged transversely—and in particular substantially perpendicularly—to the first face 13 and to the second face 14.

The base body 6 has a parallelepiped shape, the first face 13 and the second face 14 identify a first pair of opposite faces of the aforesaid parallelepiped and the side face 18 and the further side face 20 define a further pair of opposite faces of the aforesaid parallelepiped.

The base body 6 further comprises a cavity 21 having an opening 23 obtained in the face 13.

The base body 6 further comprises a further cavity 22 having a further opening 24 obtained in the face 13.

The cavity 21 and the further cavity 22 extend substantially parallel to the side face 18 and to the further side face 20. The light-emitting device 3 further comprises a first mirror and a second mirror 26 arranged, respectively, for deviating a luminous radiation generated by the first LED 4 and a luminous radiation generated by the second LED 5.

The first mirror 25 and the second mirror 26 are shaped in such a way as to be received respectively in the cavity 21 and in the further cavity 22.

The first mirror 25 and the second mirror 26 may have the shape of prisms, in particular of prisms having bases in the shape of a rectangular isosceles triangle.

The first mirror 25 and the second mirror 26 are housed in the cavity 21 and in the further cavity 22, respectively, in such a way that the aforesaid prisms have a first side face arranged substantially parallel to a plane that is orthogonal to the optical axis A, a second lateral face 28 arranged substantially perpendicularly to the aforesaid plane that is orthogonal to the optical axis A and a third side face 29—that deviates the luminous radiation generated by the first LED 4, or by the second LED 5—arranged in such a way as to form an angle that is substantially equal to 45° with respect to the aforesaid plane that is orthogonal to the optical axis A.

In particular, the first lateral face 27 is substantially parallel to the first face 13 and to the second face 14, the second lateral face 28 is substantially parallel to the side face 18 and to the further side face 20 and the third side face 29 forms an angle substantially equal to 45° with respect to the first face 13 and to the second face 14.

Alternatively, the second lateral face 28 is positioned with respect to the first lateral face 27 by a preset obtuse angle to prevent the generation of internal luminous reflections that could terminate on the sensor. In order to prevent such reflections it is further possible also to provide solutions on the internal surfaces (second lateral face 28) of the prisms such as, for example, creating great roughness to achieve greater diffusion of light.

The light-emitting device 3 further comprises a first supporting element 30 to which the first LED 4 is fixed and a second supporting element 31 to which the second LED 5 is fixed.

The first supporting element 30 may be connected to the base body 6, for example by screws 32 engaging in threaded holes obtained in the base body 6. Between the first supporting element 30 and the base body 6 elastic rings 33 are interposed that are provided with a hole through which a stem of the screws 32 passes.

The first supporting element 30 is arranged substantially parallel to the side face 18. In this way, a luminous radiation is emitted by the first LED 4 along a direction that is transverse to the optical axis A until interacting with the third side face 29 of the first mirror 25 and is deviated from the third side face 29 to the detecting plane 38.

The second supporting element 31 may be connected to the base body 6, for example by further screws 34 engaging in threaded holes obtained in the base body 6. Between the second supporting element 31 and the base body 6 further elastic rings 35 are interposed that are provided with a hole through which a stem of the further screws 34 passes.

The second supporting element 31 is arranged substantially parallel to the further side face 20. In this way, a luminous radiation is emitted by the second LED 5 along a direction that is transverse to the optical axis A until interacting with the third side face 29 of the second mirror 26 and is deviated from the third side face 29 to the detecting plane 38.

By moving the first supporting element 30 towards or away from the side face 18 it is possible to vary the distance of the first LED 4 from the first mirror 25. The first supporting element 30 may be moved towards and/or away from the side face 18 by adjusting the screws 32.

By moving the second supporting element 31 towards or away from the further side face 20 it is possible to vary the distance of the second LED 5 from the second mirror 26. The second supporting element 31 may be moved towards and/or away from the further side face 20 by acting on the further screws 34.

The vision system 1 further comprises an objective 36 having an optical axis coinciding with the axis A and arranged for focussing an image of the object on the sensor 2. The objective 36 is provided with adjusting means, which is not shown, that enables focussing to be adjusted. The objective 36 is moreover provided with further adjusting means, which is not shown, which enables the quantity of light and the depth of field of the vision system to be adjusted. The further adjusting means acts on a diaphragm of the objective. In particular, the adjusting means and the further adjusting means may comprise nuts that are drivable manually by a user, or nuts that are driven and are adjustable through suitable control devices. Advantageously, the objective 36 may be chosen from a plurality of commercial C-mount objectives on the basis of different acquisition needs.

Figure 5:
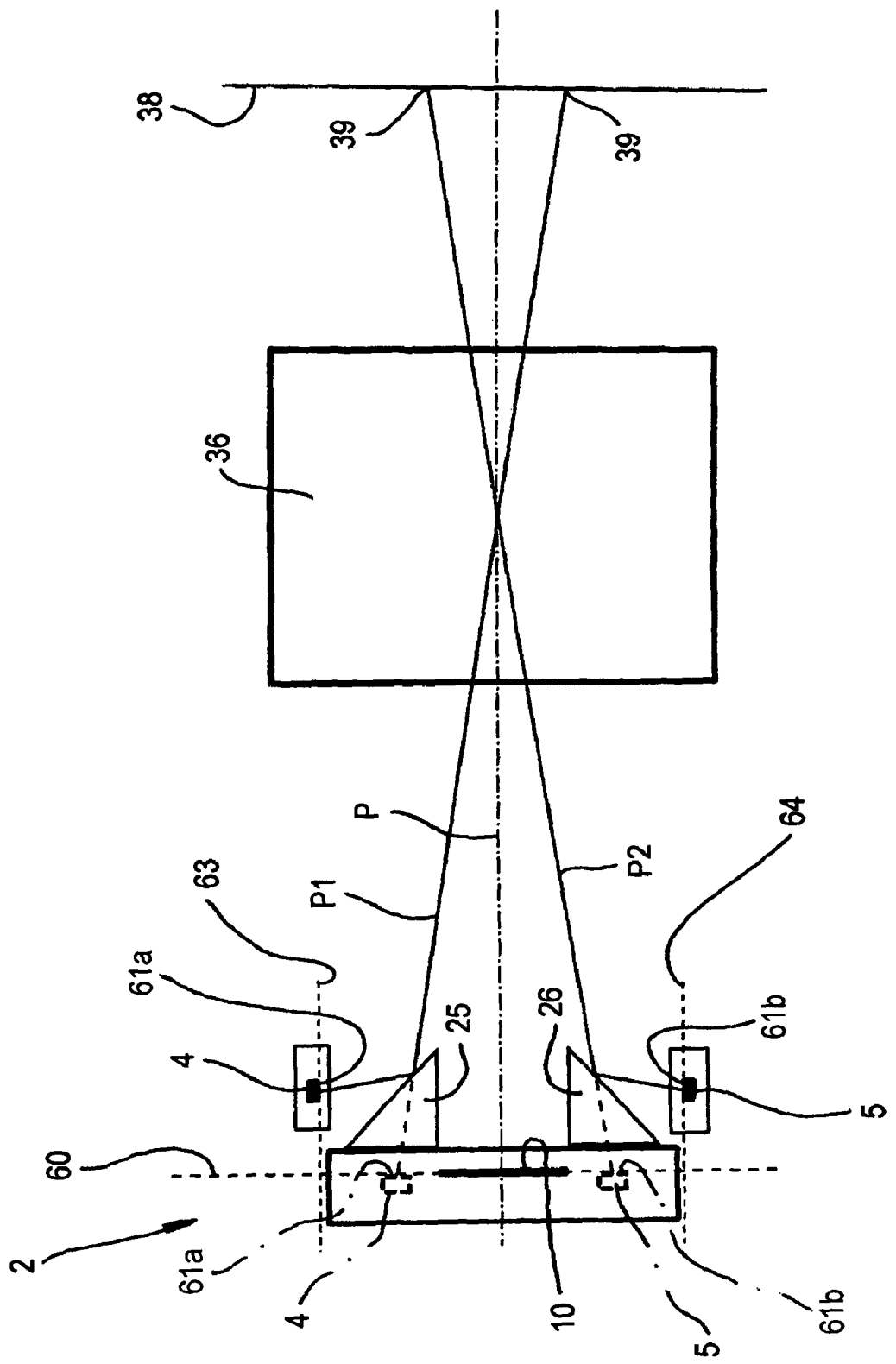
FIG. 5 is a schematic longitudinal section of the vision system in FIG. 1.

As shown in FIG. 5, between the sensor 2—i.e. between the sensitive surface 10—and the detecting plane 38 there is defined an optical path P that passes through the objective 36.

Furthermore, between the first LED 4—i.e. between the first emission surface 61a—and the detecting plane 38 there is defined a further optical path P1 and between the second LED 5—i.e. between the emission surface 61b—and the detecting plane 38 there is defined a still further optical path P2. The further optical path P1 and the still further optical path P2 pass through the objective 36.

During production of the vision system 1, the sensitive surface 10 of the sensor 2 is positioned on an image plane 60 generated by the objective 36, the emission surface 61a of the first LED 4 is positioned on a plane 63, which is a mirror plane with respect to the image plane 60, and the emission surface 61b of the second LED 5 is positioned on a further plane 64, which is a mirror plane with respect to the image plane 60.

The first mirror 25 and the second mirror 26 deviate respectively portions of luminous radiation coming from the detecting plane 38 that passes through the objective 36 in such a way that the image is formed on the plane 63 and on the further plane 64, which are arranged opposite one another with respect to the image plane 60 (thus the plane 63 and the further plane 64 are said mirror planes of the image plane 60). In particular, as the first mirror 25 and the second mirror 26 are tilted by 45° with respect to the image plane 60, which is arranged substantially perpendicularly with respect to the optical axis A, the plane 63 and the further plane 64 are arranged substantially parallel to the optical axis A.

The first mirror 25 and the second mirror 26 reflect respectively the luminous radiation emitted by the first LED 4 and by the second LED 5.

Owing to the first mirror 25 and to the second mirror 26, although in fact the first LED 4 and the second LED 5 are positioned to the side of the sensor 2, an operating configuration is created that corresponds to having the emission surface 61a of the first LED 4 and the emission surface 61b of the second LED 5 positioned exactly on the same plane as the sensitive surface 10 of the sensor 2—i.e. on the image plane 60—as shown with a broken line in FIG. 5.

In fact, the first mirror 25 and the second mirror 26 generate the mirror image of the emission surface 61a of the first LED 4 and of the emission surface 61b of the second LED 5 on the image plane 60.

An operating configuration is thus made in which the mirror image of the emission surface 61a of the first LED 4 and the mirror image of the emission surface 61b of the second LED 5 are on the same plane in which the sensitive surface of the sensor 10 is positioned, i.e. on the image plane 60.

As the optical path P, the further optical path P1 and the still further optical path P2 pass through the objective 36 and as the sensitive surface 10 of the sensor 2 is on the image plane 60, the emission surface 61a of the first LED 4 is on the plane 63, which is a mirror plane with respect to the image plane 60, and the emission surface 61b of the second LED 5 and on the further plane 64, which is a mirror plane with respect to the image plane 60 (i.e. the emission surface 61a of the first LED 4 and the emission surface 61b of the second LED 5 are positioned virtually on the image plane 60 on which the sensitive area 10 is also positioned), it is provided that when the detecting plane 38 is focussed on the sensor 2, the luminous reference FIG. 39 is perceived visually focussed on the detecting plane 38 by an operator who observes the luminous reference FIG. 39 with the naked eye.

During installation of the vision system 1 this enables the focussing of the sensor 2 to be easily checked and adjusted.

The vision system 1 may be assembled in the way disclosed below.

The base body 6 is fixed to the plate 12, which accommodates the sensor 2 in such a way that the package 8 is received in the seat 7 in a shapingly coupled manner, which enables centering of the sensor 2 with respect to the base body 6 to be assured.

The first mirror 25 and the second mirror 26 are housed in the cavity 21 and in the further cavity 22, respectively, and fixed to the base body 6 by fixing means, which is not shown. The first supporting element 30 is associated with the base body 6 in such a way that the first LED 4 is received in the first gap 15.

Similarly, the second supporting element 31 is associated with the base body 6 in such a way that the second LED 5 is received in the second gap 16.

The first mirror 25, the second mirror 26, the first supporting element 30 and the second supporting element 31 can be associated with the base body 6 before the base body 6 is connected to the plate 12, or after the base body 6 has been connected to the plate 12.

The objective 36 is fixed to a cover 87 of the external enclosure 56 of the vision system 1. The enclosure 56 further comprises an enclosure body 86 to which the cover 87 may be connected, for example by screws.

Further, the vision system 1 is equipped with the illuminating device 80 arranged for illuminating the objects to be detected.

During the manufacturing step (production and calibration) the relative positioning of the sensor 2, of the first LED 4 and of the second LED 5 is carried out in the manner disclosed below.

Above all, positioning the vision system 1 at a preset distance from the detecting plane 38 and activating the sensor 2 to detect a sample image is provided.

Subsequently, the objective 36 is adjusted using the adjusting means until the sample image is viewed focussed by the sensor 2, i.e. until the sensitive surface 10 lies on the image plane 60.

In order to evaluate the degree of focussing of the sample image it is possible to make a series of measurements and examine these measurements, for example in the form of photographs that are displayed on a display of the vision system 1 of a computer connected to the vision system 1. Subsequently, the light-emitting device is switched on to generate the luminous reference FIG. 39 on the light-emitting device.

Subsequently, the first LED 4 is moved towards or away from the first mirror 25 and the second LED 5 is moved towards or away from the second mirror 26 until a configuration is reached in which the luminous reference FIG. 39—i.e. the luminous image generated by the first LED 4 and the further luminous image generated by the second LED 5—appears to be visually focussed on the detecting plane 38.

The first LED 4 may be moved towards or away from the first mirror 25 by screwing or unscrewing the screws 32 with respect to the base body 6.

Similarly, the second LED 5 may be moved towards or away from the second mirror 26 by screwing or unscrewing the further screws 34 with respect to the base body 6.

When the luminous image generated by the first LED 4 and the further luminous image generated by the second LED 5 appear focussed on the detecting plane 38 this means that the emission surface 61a of the first LED 4 is on the plane 63 which is a mirror plane of the image plane 60 and the emission surface 61b of the second LED 5 is on the further image plane 64 which is a mirror plane of the image plane 60. The first LED 4 and the second LED 5 are thus maintained in the positions reached at the end of the adjusting step disclosed above.

The first supporting element 30 and the second supporting element 31 enable fine adjustment of the position of the first LED 4 and of the second LED 5, i.e. fine adjustment of a distance of the first LED 4 from the first mirror 25 and of a further distance of the second LED 5 from the second mirror 26.

Fine adjustment of the aforesaid distance and of the aforesaid further distance based on a visual observation of the focussing of the luminous image generated by the first LED 4 and of the further luminous image generated by the second LED 5 is much simpler than fine adjustment based on a direct measurement of the aforesaid distance and of the aforesaid further distance, this, in particular, in the light of the small dimensions of the parts that form the light-emitting device 3.

The vision system 1 may be equipped with an objective 36 selected from a group of objectives, for example to change according to necessity the width of the field of view of the sensor 2.

Installation of the vision system 1 for subsequent operational activity may be achieved in the way disclosed below.

Above all, the vision system 1 is positioned at a desired distance from the detecting plane 38 and the first LED 4 and the second LED 5 of the light-emitting device 3 are lighted. Subsequently, the objective 36 is adjusted, which is for example selected from a plurality of possible objectives on the basis of the features and needs of the specific application, by means of the adjusting means until the luminous reference FIG. 39 appears to be visually focussed on the detecting plane 38.

After installation of the vision system 1 has finished, it is possible to switch off the first LED 4 and the second LED 5 and possibly keep the first LED 4 and the second LED 5 constantly switched off.

In this way, during operation of the vision system 1, the light emitted by the first LED 4 and by the second LED 5 does not disturb the sensor 2.

Figure 17:
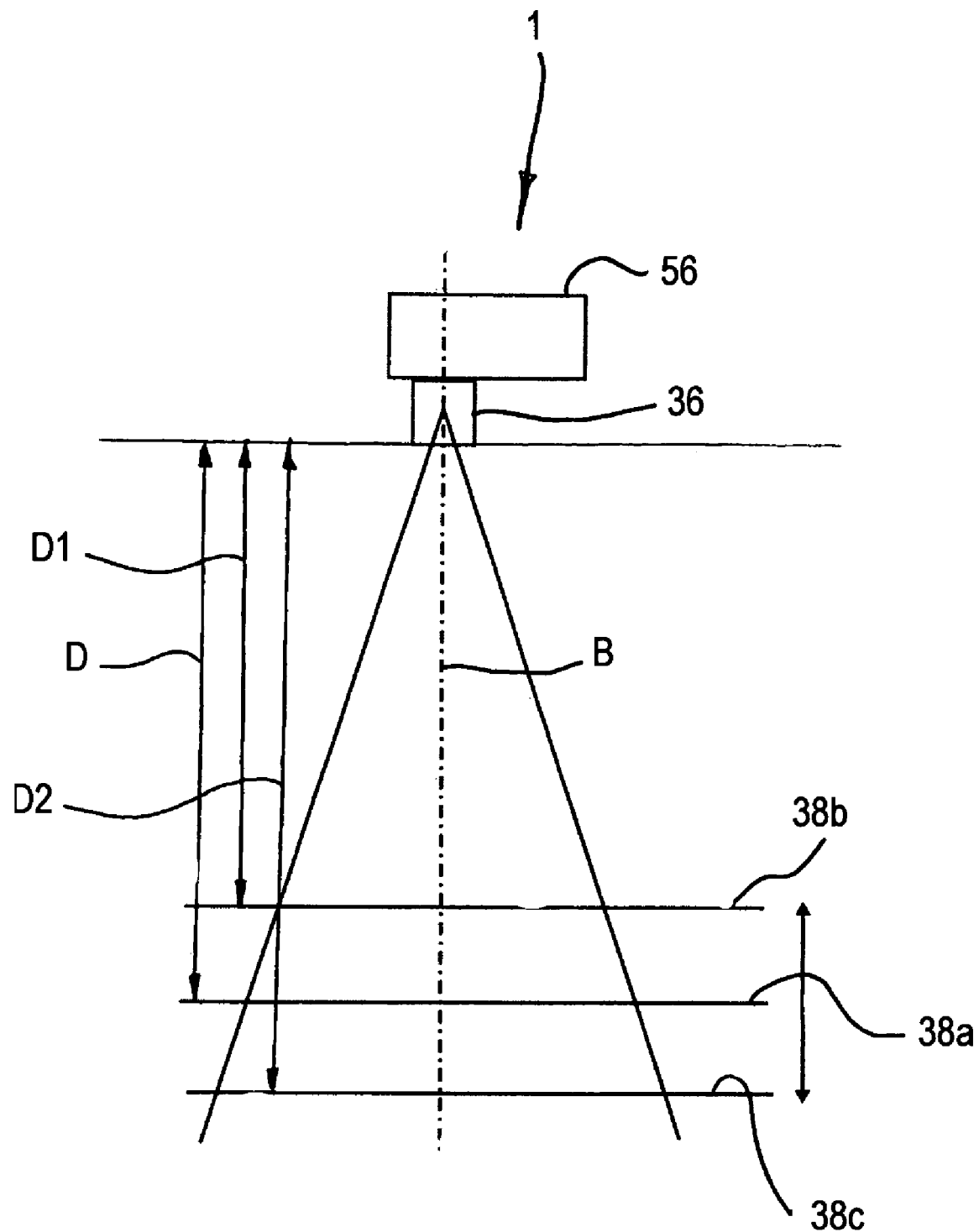
FIG. 17 is a schematic side view of a vision system.

With reference to FIG. 17 a method is disclosed for adjusting the luminosity and the depth of field of the objective 36.

The vision system 1 is installed above a conveying device, not shown, which conveys objects, for example packages. The detecting plane 38 is defined by an upper face of a package to which, for example, a barcode may be applied. The aforesaid conveyor moves packages having heights, i.e. distances from the vision system 1, belonging to a preset range.

With the diaphragm of the objective 36 completely open, in the manner disclosed above, the focussing of the objective 36 is adjusted by passing under the vision system 1 a first pack that defines a first detecting plane 38a arranged at a first distance D from the vision system 1. The distance D corresponds to an intermediate value within the aforesaid range.

Subsequently, by passing a second package below the vision system 1 that defines a second detecting plane 38b arranged at a second distance D1 from the vision system 1 it is detected whether the luminous reference FIG. 39 appears to be visually focussed on the second detecting plane 38b. The second distance D1 is less than the first distance D, i.e. the second package has a greater height than that of the first package, this height having a value near a lower end of the aforesaid range.

If the luminous reference FIG. 39 does not appear to be visually focussed on the detecting plane 38b, the luminosity and the depth of field of the objective 36 are adjusted by acting on the diaphragm of the objective 36, maintaining the focus fixed. This corresponds to a partial closure of the diaphragm of the objective 36.

Still subsequently, by passing below the vision system 1 a third package that defines a third detecting plane 38c arranged at a third distance D2 from the vision system 1, it is checked whether the luminous reference FIG. 39 appears to be visually focussed on the third detecting plane 38c. The third distance D2 is greater than the first distance D, i.e. the third package has a lower height than that of the first package, this height having a value that is near to an upper end of the aforesaid range.

If the luminous reference FIG. 39 does not appear visually focussed on the third detecting plane 38c, it is possible to further adjust the luminosity and the depth of field of the objective 36, by acting on the diaphragm of the objective 36, until the luminous reference figure appears to be visually focussed on the third detecting plane 38c. This corresponds to a partial further closure of the diaphragm of the objective 36.

Known the minimum and maximum height of the packages to be examined, it is possible, during the installation step, to adjust once and for all focussing, luminosity and depth of field of the objective 36 in such a way that images of all the packages having a height belonging to the aforesaid range are correctly acquired.

As shown in FIGS. 1 to 4, the through hole 9, the cavity 21 and the further cavity 22 are shaped in such a way that the first mirror 25 and the second mirror 26 are very near, possibly as near as possible, to the sensitive surface 10. In this way, the luminous reference FIG. 39 generated by the light-emitting device 3 provides a very precise indication of the field of view of the sensor 2.

In addition, during mounting, the luminous reference FIG. 39 may also provide an indication of the correct mutual positioning—for example of the alignment—of the vision system 1 and of the detecting plane 38.

Figures 15, 16:
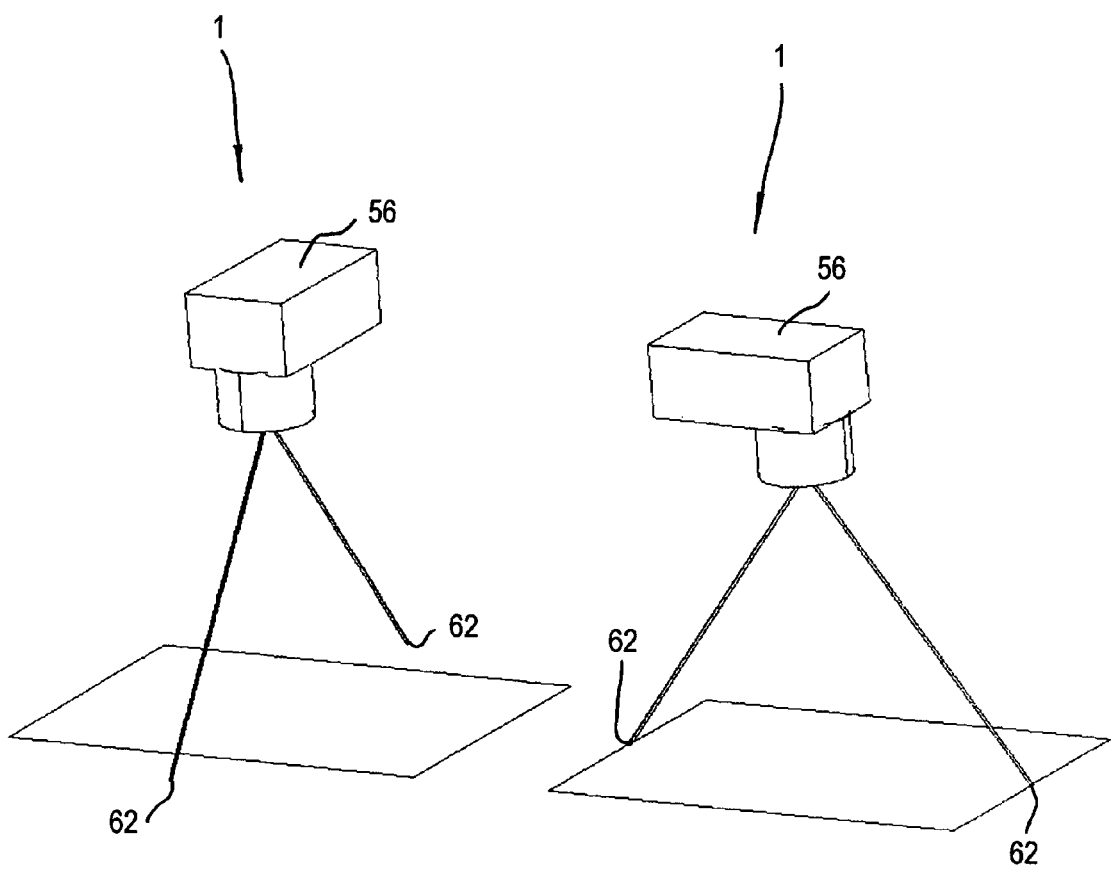
FIG. 15 is a schematic perspective view of a vision system in an operating configuration.
FIG. 16 is a view like that in FIG. 15 showing the vision system in a further operating configuration.

With reference to FIGS. 15 and 16, there is shown a vision system 1 that may be mounted in a rotatable manner on a supporting structure. In particular, the vision system can rotate around the optical axis A.

During installation, the vision system 1 is positioned in a first operating configuration. When the first LED 4 and the second LED 5 are switched on, the two luminous points 62 that define the luminous reference FIG. 39 give an indication of a first dimension of the field of view.

Subsequently, the vision system 1 is rotated by approximately 90° around the optical axis A to take on a further operating configuration, in which the luminous points 62 that define the luminous reference FIG. 39 give an indication regarding a second dimension of the field of view arranged transversely to the aforesaid first dimension.

In this way, as the vision system 1 is rotatable, it is possible to have an extremely precise indication of the position and the extent of the field of view.

In an embodiment that is not shown, the vision system 1 may comprise a number of LEDs other than 2. In particular, in addition to the first LED 4 and to the second LED 5, a third LED and a fourth LED can be provided, the third LED and the fourth LED being housed in a third gap and in a fourth gap, respectively, obtained in further side faces of the base body 6 arranged transversely with respect to the side face 18 and to the further side face 20. The first LED 4, the second LED 5, the third LED and the fourth LED surround, in this case, the sensitive surface 10. Alternatively, instead of the first LED 4 and the second LED 5 a single LED may be provided.

With reference to FIGS. 6 to 9, embodiments of the vision system 1 are shown comprising a beam splitter 40.

Figure 6:
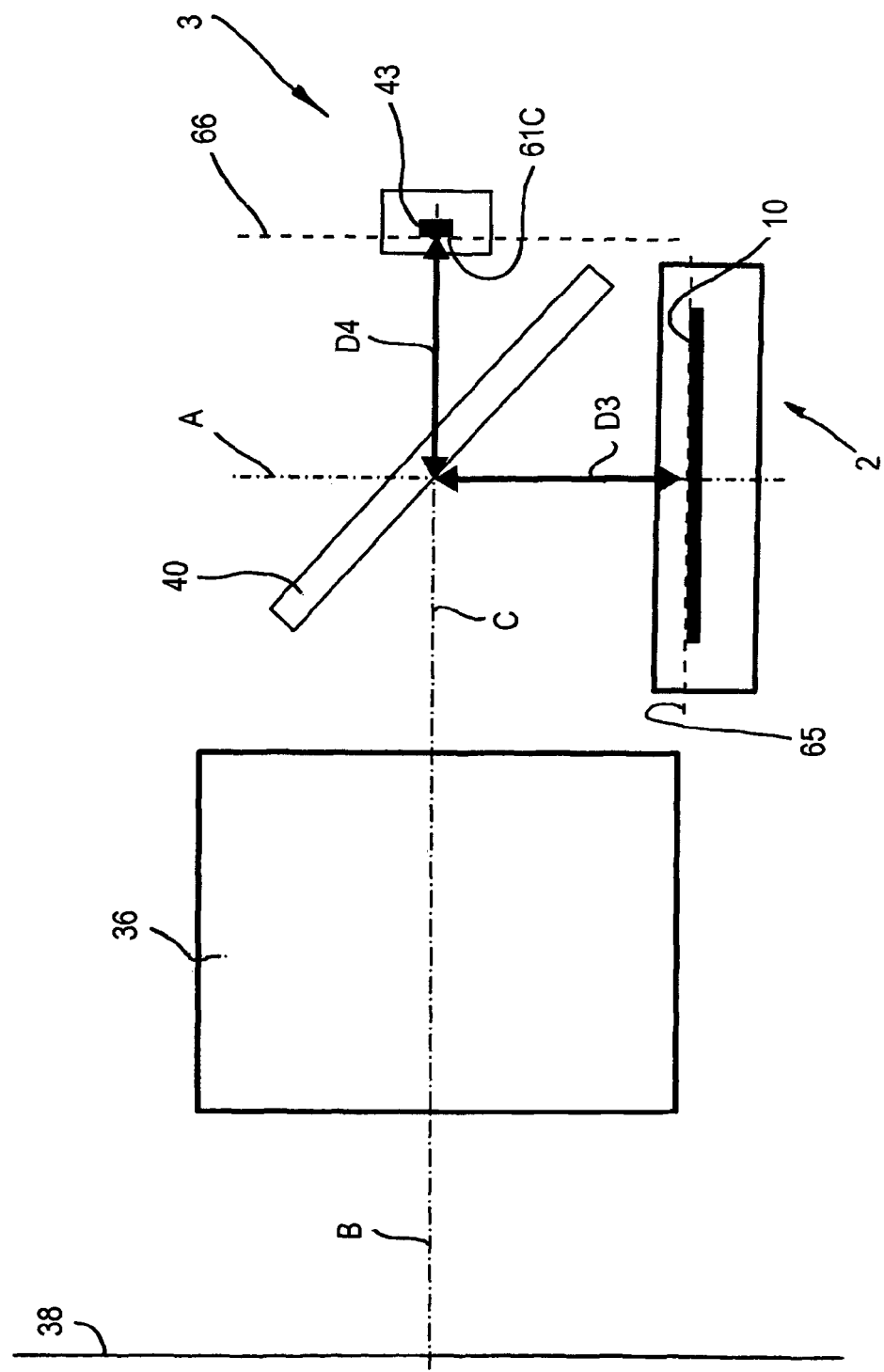
FIG. 6 is a schematic longitudinal section of a vision system made according to a version.
Figure 7:
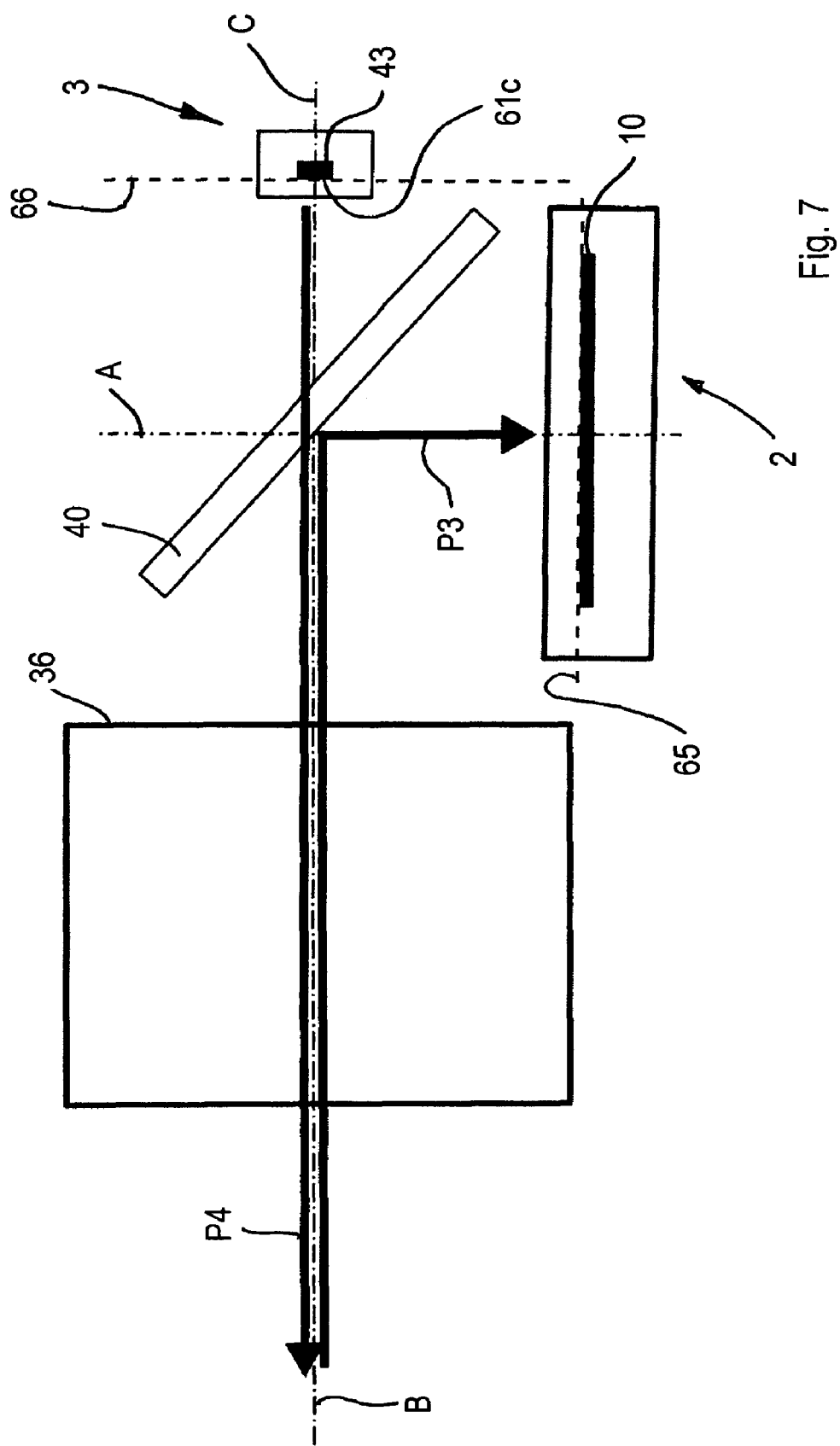
FIG. 7 is a section like the one in FIG. 6 showing an optical path defined between a sensor of the vision system and an object and a further optical path defined between a light-emitting device of the vision system and the object.

As shown in FIGS. 6 and 7, a first version of the vision system 1 comprises a light-emitting device 3, provided with a light source, for example a LED 43 having an emitting axis C aligned with an optical axis B of the objective 36, and a sensor 2 having an optical axis A arranged transversely to the optical axis B. In particular the optical axis A is arranged substantially perpendicularly to the optical axis B. The beam splitter 40 creates a plane 65 which is a mirror plane of the image plane 66 generated by the objective 36. An emission surface 61c of the led 43 is positioned on the image plane 66 and a sensitive surface 10 of the sensor 2 is positioned on the plane 65.

The image plane 66 is arranged substantially perpendicularly to the optical axis B, whilst the plane 65—generated by the beam splitter 40—is arranged substantially parallel to the optical axis B.

The sensor 2, the beam splitter 40 and the LED 43 are positioned in such a way that a distance D3 of the sensitive surface 10 of the sensor 2 from the beam splitter 40, measured perpendicularly to the optical axis B, is the same as a further distance D4 of the emission surface 61c of the LED 43 from the beam splitter 40, measured along the optical axis B. This neglecting the internal refractions of the beam splitter 40.

Between the detecting plane 38 and the sensitive surface 10 of the sensor 2 there is defined an optical path P3 that passes through the objective 36.

Between the emission surface 61c of the LED 43 and the detecting plane 38 there is defined a further optical path P4 that passes through the objective 36.

The beam splitter 40 deviates the optical path P3, but does not deviate the further optical path P4.

The length of the further optical path P4 measured along the optical axis B is the same as the length of the optical path P3 measured along the optical axis B and the emission axis C. This neglecting the internal refractions of the beam splitter 40.

Figure 8:
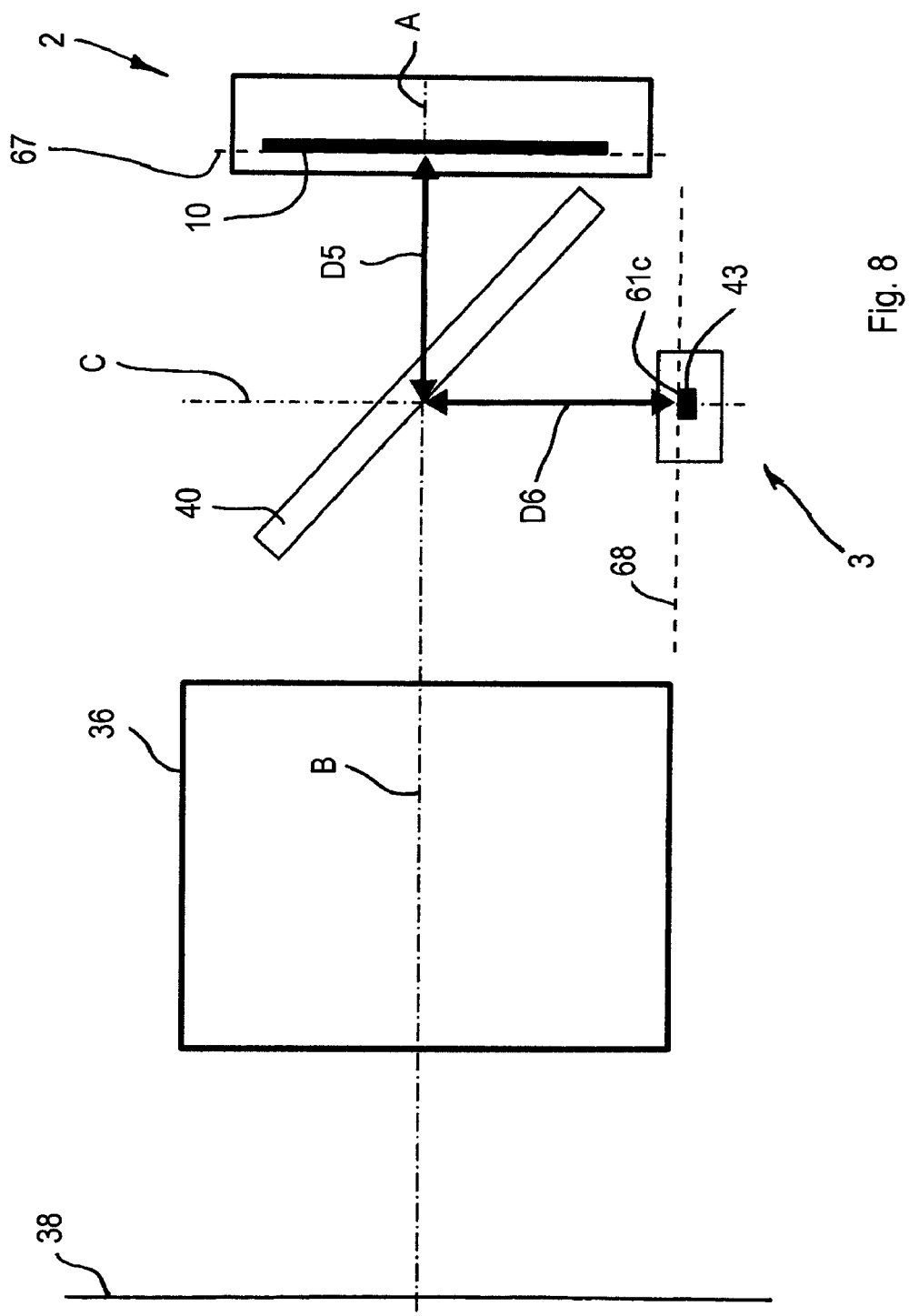
FIG. 8 is a schematic longitudinal section of a vision system manufactured according to a further version.
Figure 9:
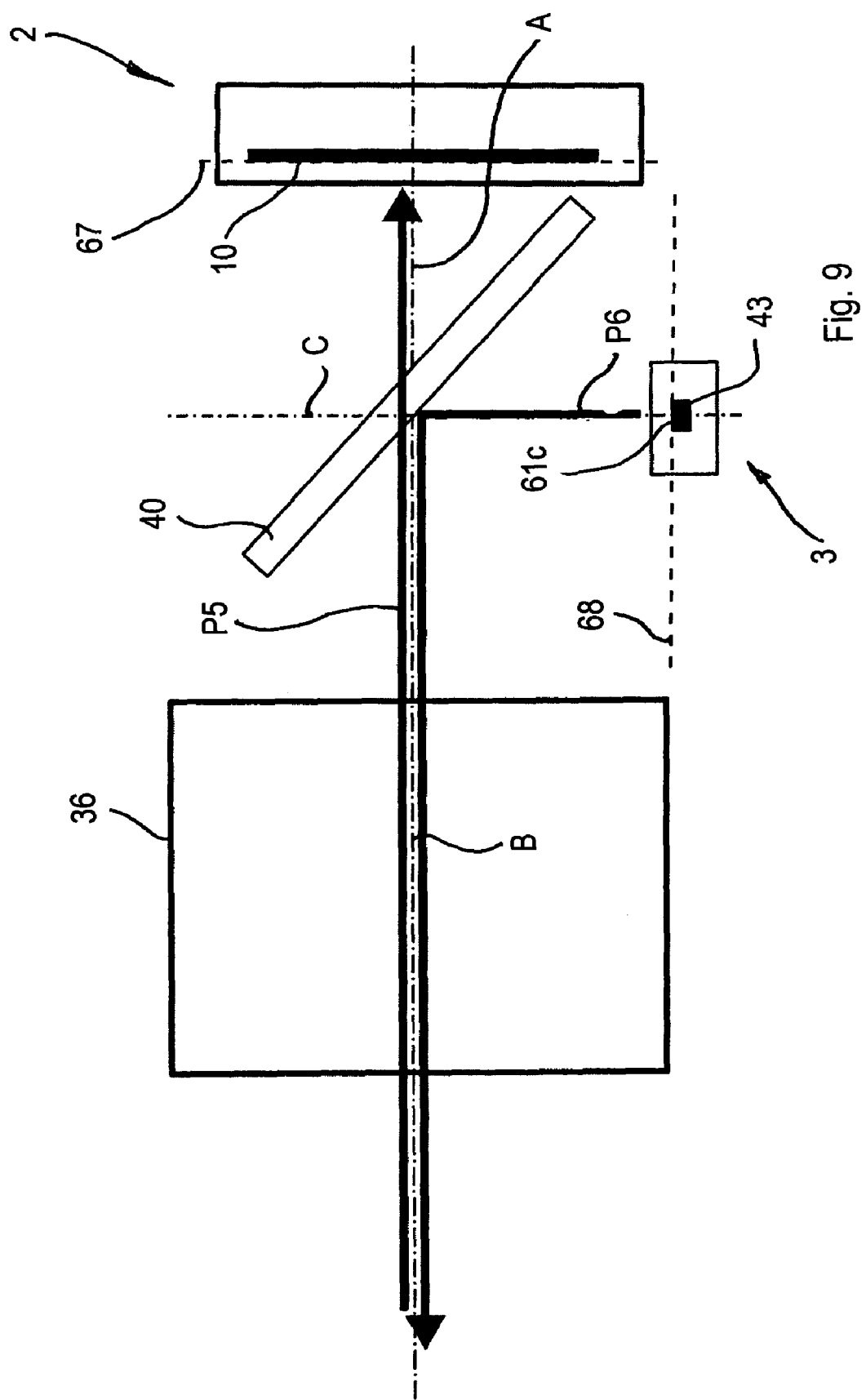
FIG. 9 is a section like the one in FIG. 8 showing an optical path defined between a sensor of the vision system and an object and a further optical path defined between a light-emitting device of the vision system and the object.

As shown in FIGS. 8 and 9, a second variation of the vision system 1 comprises a sensor 2 having an optical axis A aligned with an optical axis B of the objective 36, and a light-emitting device 3, provided with a light source, for example a LED 43 having an emitting axis C arranged transversely to the axis B. In particular the emission axis C is arranged substantially perpendicularly to the optical axis B.

The beam splitter 40 creates a plane 68 which is a mirror plane of the image plane 67 generated by the objective 36. A sensitive surface 10 of the sensor 2 is positioned on the image plane 67 and an emission surface 61c of the LED 43 is positioned on the plane 68.

The image plane 67 is arranged substantially perpendicularly to the optical axis B, whilst the plane 68—generated by the beam splitter 40—is arranged substantially parallel to the optical axis B.

The sensor 2, the beam splitter 40 and the LED 43 are positioned in such a way that a distance D5 of the sensitive surface 10 of the sensor 2 from the beam splitter 40, measured along the optical axis B, is the same as a further distance D6 of the emission surface 61c of the LED 43 from the beam splitter 40, measured perpendicularly to the optical axis B. This neglecting the internal refractions of the beam splitter 40.

Between the detecting plane 38 and the sensitive surface 10 of the sensor 2 there is defined an optical path P5 that passes through the objective 36.

Between the emission surface 61c of the LED 43 and the detecting plane 38 there is defined a further optical path P6 that passes through the objective 36.

The beam splitter 40 deviates the further optical path P6, but does not deviate the optical path P5.

The length of the optical path P5 measured along the optical axis B is the same as the length of the further optical path P6 measured along the optical axis B and the emission axis C. This neglecting the internal refractions of the beam splitter 40.

The beam splitter 40 may comprise a semitransparent mirror. Alternatively, the beam splitter 40 may comprise a dichroic mirror.

A dichroic mirror is an accurate optical filter that selectively lets through the incident light within a certain range of wavelengths whilst reflecting the others.

The dichroic mirror is transparent to a luminous radiation coming from the object and directed to the sensor, but reflects a further luminous radiation coming from the LED and directed to the object or vice versa.

Using a beam splitter enables numerous advantages to be obtained, such as:
- projecting information inside the FoV;
- using any number of LEDs at will;
- the possibility of using emitting displays (for example with OLEDs technology) in such a way as to display luminous reference figures of any shape, or the possibility of displaying messages or indications of good reading or in response to acquisition;
- the possibility that the zone defined by the luminous reference figure corresponds exactly to the field of view of the sensor;
- the possibility of further simplifying the structure and the manufacture of the vision system.

Also in the embodiments of the vision system 1 in FIGS. 6 to 9 adjusting means is provided that, similarly to the screws 32 and to the further screws 34 disclosed with reference to the embodiment of the vision system 1 in FIGS. 1 to 5, enables the position of the LED 43 and/or of the sensor 2 and/or of the beam splitter 40 to be adjusted. Adjusting (calibrating) occurs in all embodiments except for those of FIGS. 10, 11, 13, 14 and 18 which will be disclosed below.

Figure 10:
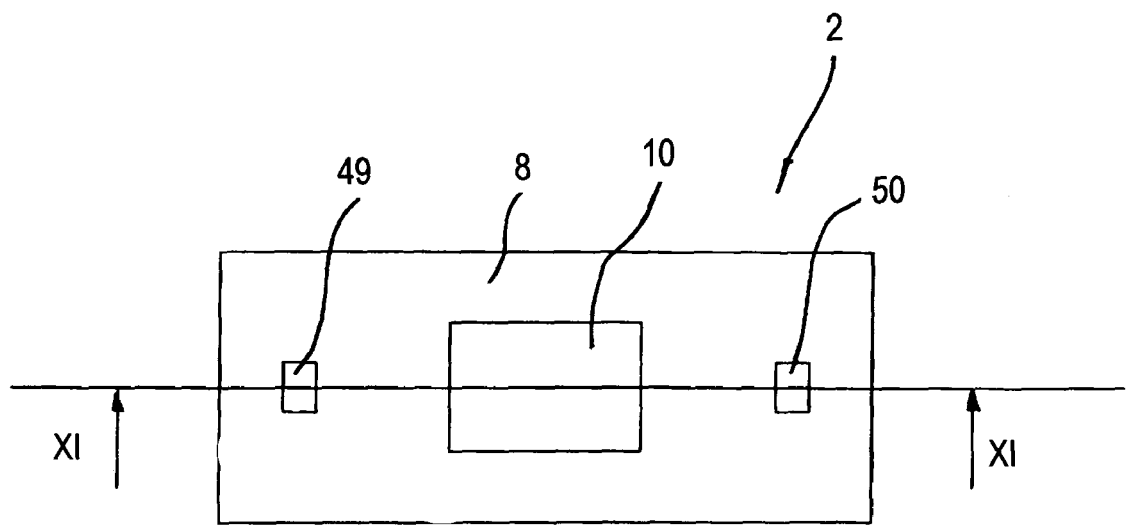
FIG. 10 is a schematic plan view of a sensor of a vision system manufactured according to a still further version.
Figure 11:
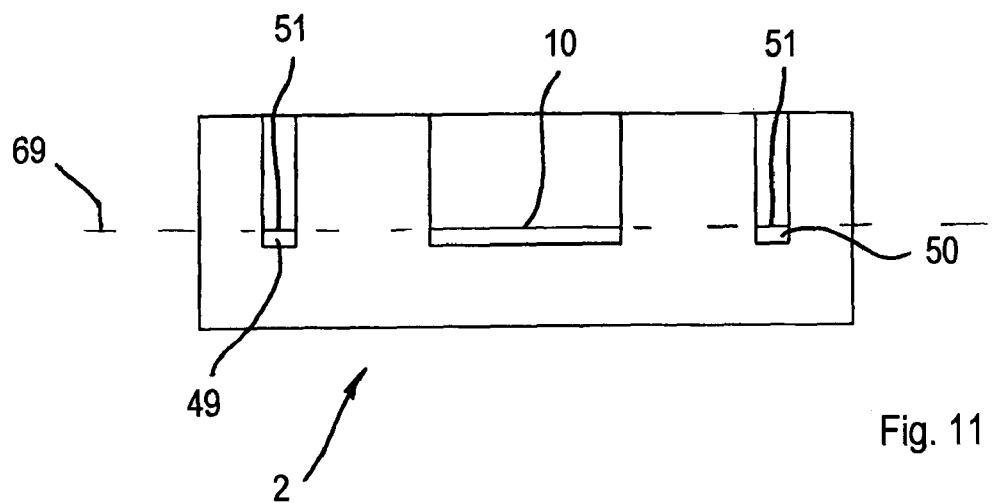
FIG. 11 is a section taken along a plane XI-XI in FIG. 10.

With reference to FIGS. 10 and 11, an embodiment of the vision system 1 is shown in which a first LED 49 and a second LED 50 are recessed in the package 8 of the sensor 2 in such a way that emission surfaces 51 of the first LED 49 and of the second LED 50 are coplanar with the sensitive surface 10 of the sensor 2.

In this case, when the detecting plane 38 is focussed by the objective 36, the sensitive surface 10 and the emission surfaces 51 of the first LED 49 and of the second LED 50 lie on the image plane 69 generated by the objective 36.

Figure 18:
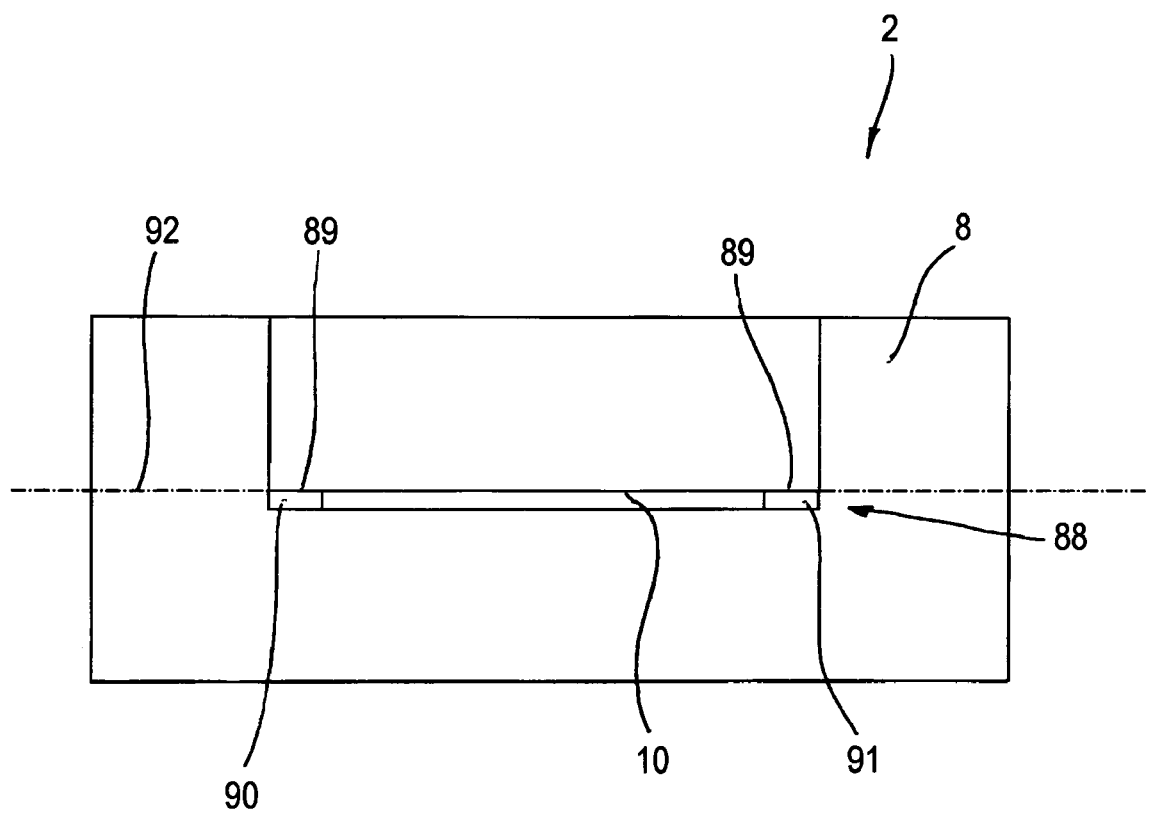
FIG. 18 is a schematic cross section of a sensor of a vision system made according to a version.

With reference to FIG. 18, an embodiment of the vision system 1 is shown in which the package 8 of the sensor 2 comprises on the same substratum 88 the sensitive surface 10 and emission surfaces 89 of a first LED 90 and of a second LED 91.

In this case, when the detecting plane 38 is focussed by the objective 36, the sensitive surface 10 and the emission surfaces 89 of the first LED 90 and of the second LED 91 lie on the same image plane 92 generated by the objective 36.

It is therefore possible to obtain a precise indication of an extension of the FoV, as the first LED 90 and the second LED 91 are adjacent to the sensitive area 10 of the sensor 2.

Figure 13:
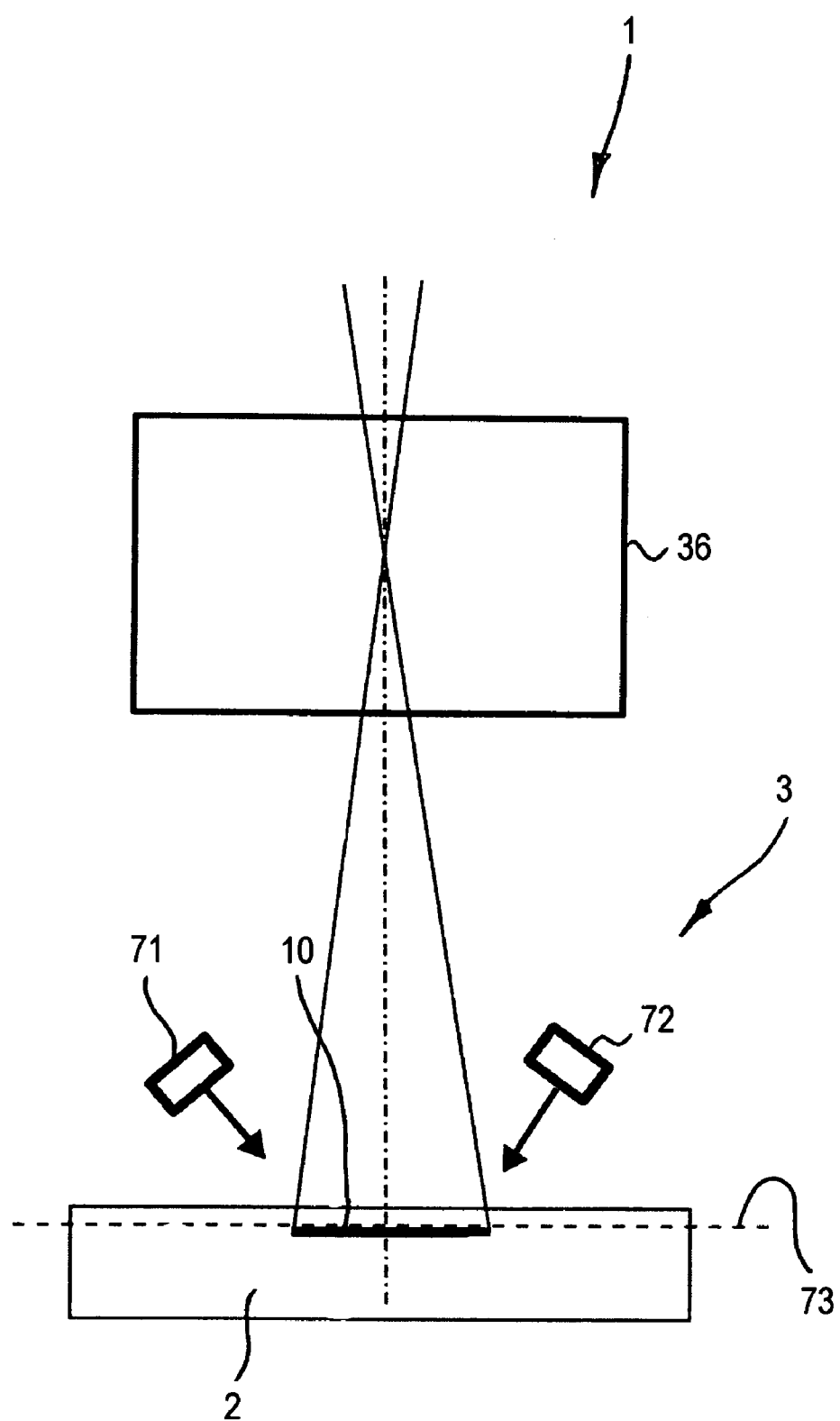
FIG. 13 is a schematic longitudinal section of a vision system made according to a still further version.
Figure 14:
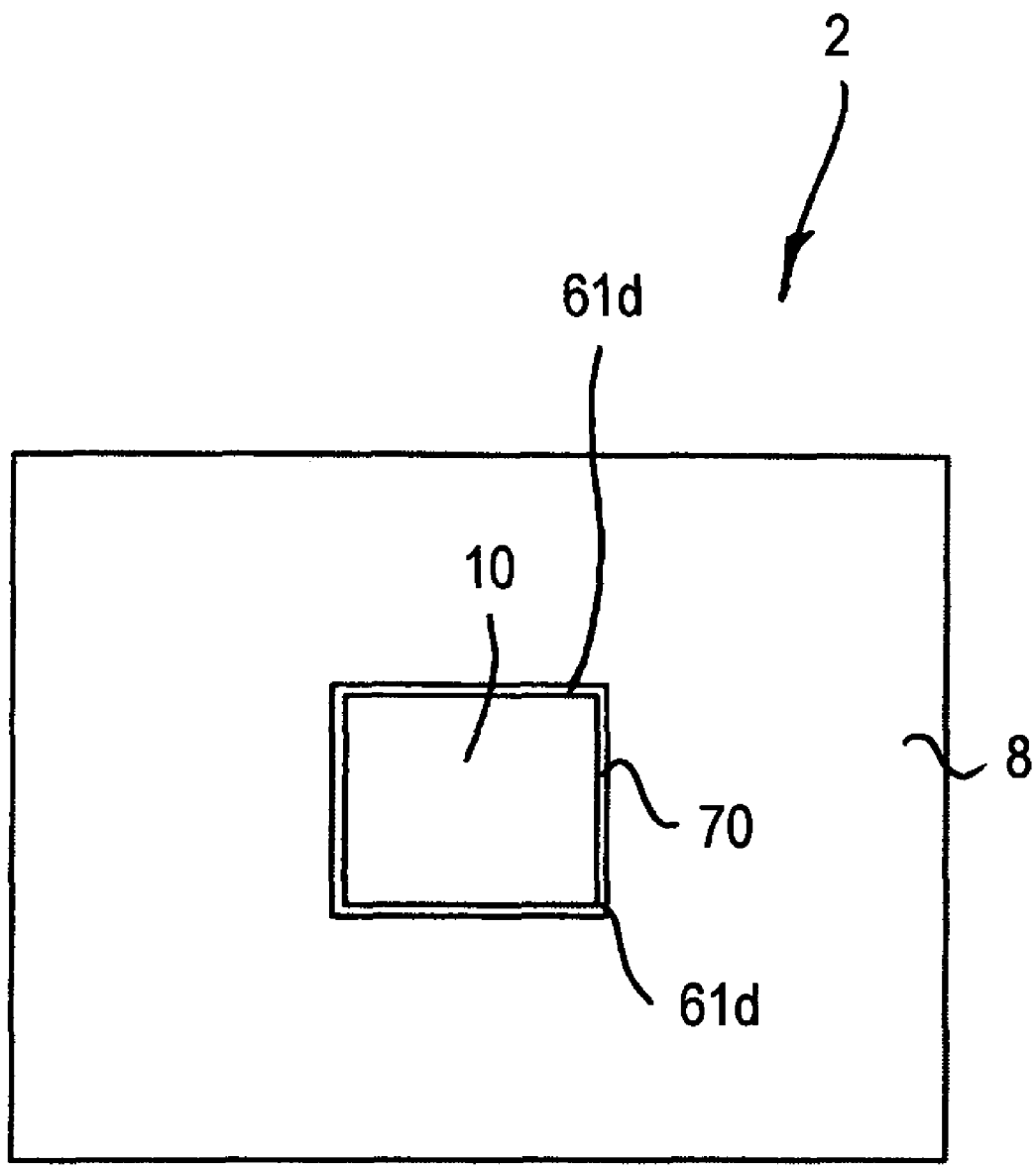
FIG. 14 is a plan view of a sensor of the vision system in FIG. 13.
Figure 21:
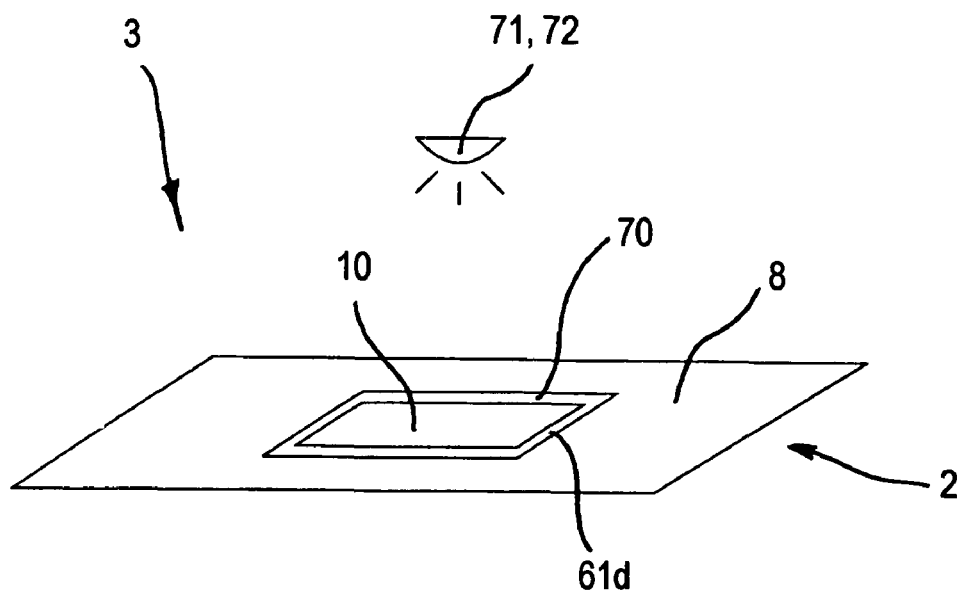
FIG. 21 is a perspective schematic view of the light-emitting device shown in FIGS. 13 and 14.

With reference to FIGS. 13, 14 and 21, an embodiment of the vision system 1 is shown that is provided with a sensor 2 having a package 8, a sensitive surface 10 and a reflecting frame 70 that surrounds the sensitive surface 10. This frame 70 is an integral part of the commercial CCD and CMOS sensors and typically comprises the metallisation and the bondings of the chips of the aforesaid sensors.

The sensitive surface 10 and the frame 70 lie on the same plane.

The vision system 1 further comprises a first LED 71 and a second LED 72 that emits a luminous radiation to the frame 70.

The luminous radiation emitted by the first LED 71 and by the second LED 72 and reflected by the frame 70 generates on the detecting plane 38 a reference image 39 corresponding to the FoV of the sensor 2.

In this case, the frame 70, by cooperating with the first LED 71 and with the second LED 72, defines the light-emitting device 3. The frame 70 defines an emission surface 61d of the light-emitting device 3.

The sensitive surface 10 and the frame 70 are on the same image plane 73 generated by the objective 36.

In the embodiments of the vision system 1 shown in FIGS. 10 and 11, 13 and 14, and 18 to 22, therefore, beam-deviating means is not present that deviates the luminous radiation coming from the object and directed to the sensor and or the luminous radiation coming from the light-emitting device and directed to the object, these beam deviating means being on the other hand provided, in the embodiment of the vision system 1 shown in FIGS. 1 to 5 in the shape of the first mirror 25 and of the second mirror 26, and in the embodiments of the vision system 1 shown in FIGS. 6 to 9 in the shape of the beam splitter 40.

The light emitting device 3 may comprise one or more LEDs having preset bonding, in such a way that the luminous figures generated by the aforesaid LEDs have a shape that is such as to simplify visual evaluation of the focussing.

Figure 12:
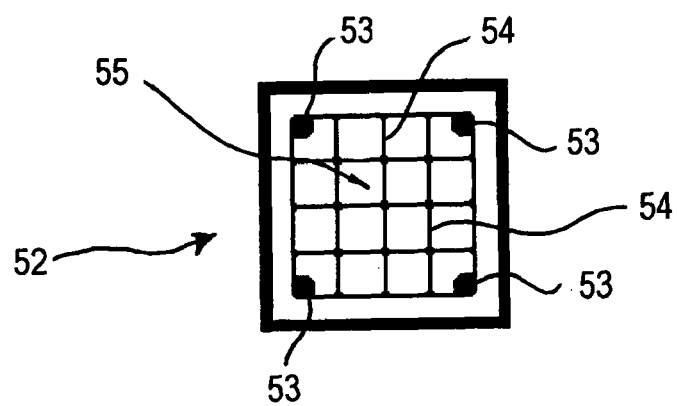
FIG. 12 is a plan view of a LED of an emitting device of a vision system.

As shown in FIG. 12, the LED may comprise a quadrilateral-shaped chip 52 provided with four bondings 53 arranged at the tops of the aforesaid quadrilateral and a plurality of metallization lines 54 arranged for forming a grid 55. The chosen emission surface of the LED is the upper one of the chip. The luminous figure generated by the chip 52 through the objective 36 has a grid shape that enables a simpler evaluation of the focussing with respect to the case of the luminous figures constituted by a single point.

Alternatively, in the light-emitting device at least a LED with a plastic package of, for example, 5 mm may be provided. The "emission surface" of a LED of this type does not generally coincide with the luminous emission zone of the chip, due to the presence of interposed optics (the dome lens of the package).

Alternatively, in the light-emitting device there may be provided at least a LED that generates a luminous point, between the LED and the object there being interposed a mask arranged for transforming the luminous point into a luminous reference figure having a desired shape.

The "emission surface" of the emitting device is in this case the surface of the mask, inasmuch as the objective focuses this mask and not the LED. Also in this case, the particular shape of the aforesaid outline facilitates a visual evaluation of the focussing of the luminous reference figure. In general, the light-emitting device 3 may comprise a variety of emission surfaces.

Figure 20:
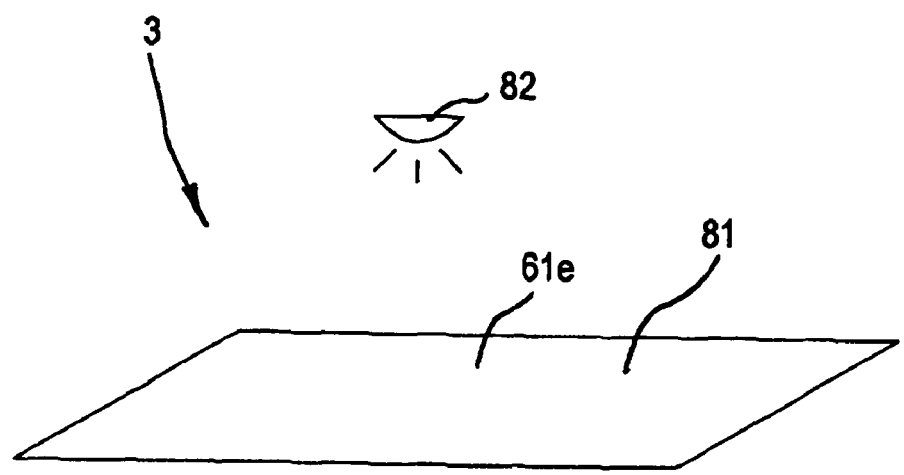
FIG. 20 is a perspective lateral view of a light-emitting device of a vision system.

As shown in FIG. 20, the light-emitting device 3 may comprise a transparent or semi-transparent support 81 on which graphic information of any type or shape is shown (for example slides) associated with a light source 81. The transparent or semi-transparent support defines an emission surface 61e of the light-emitting device 3.

Figure 22:
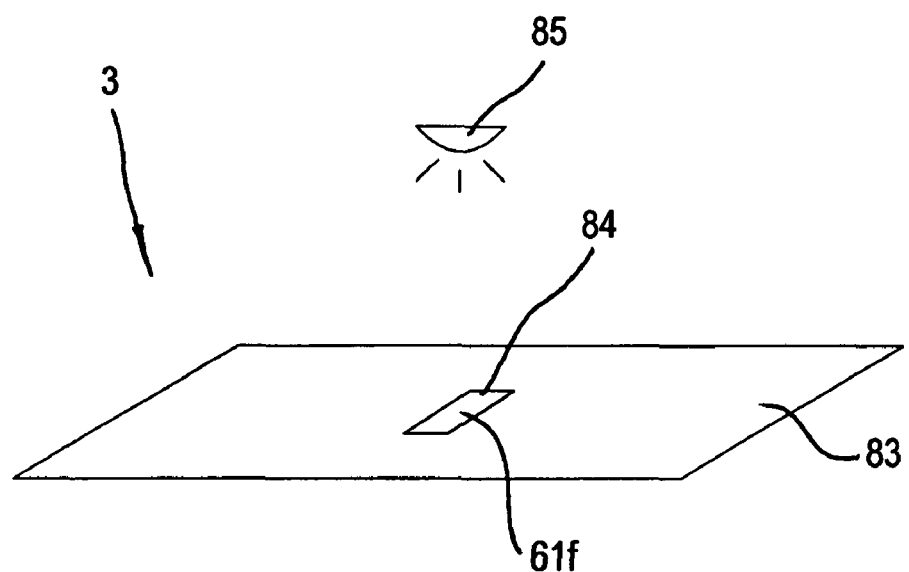
FIG. 22 is a schematic perspective view of a light-emitting device made according to a version.
Figure 23:
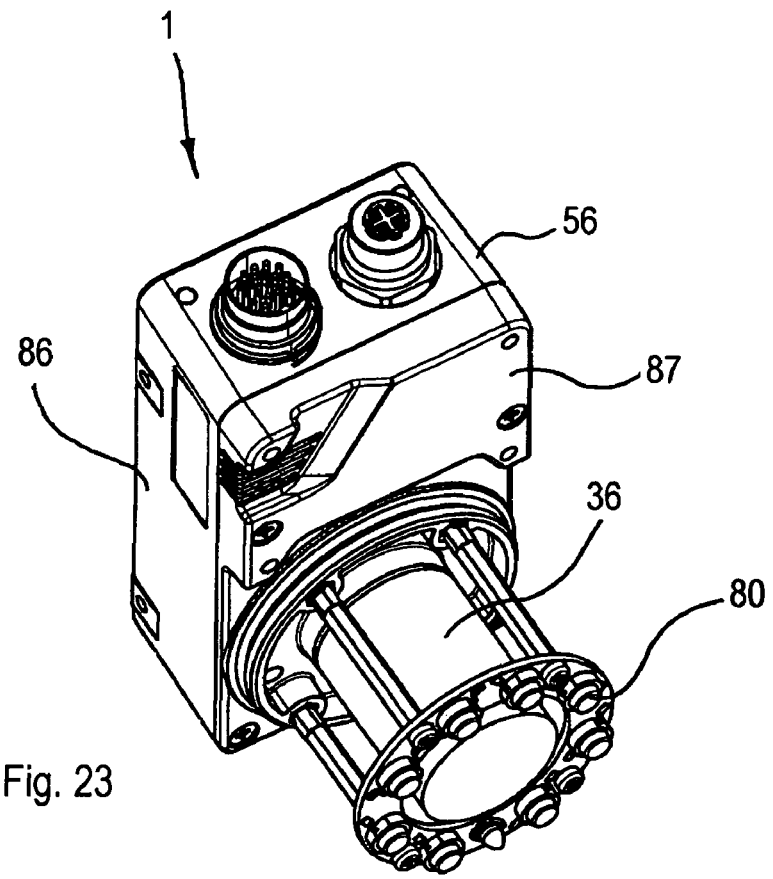
FIGS. 23 to 26 are perspective views of a vision system.
Figure 24:
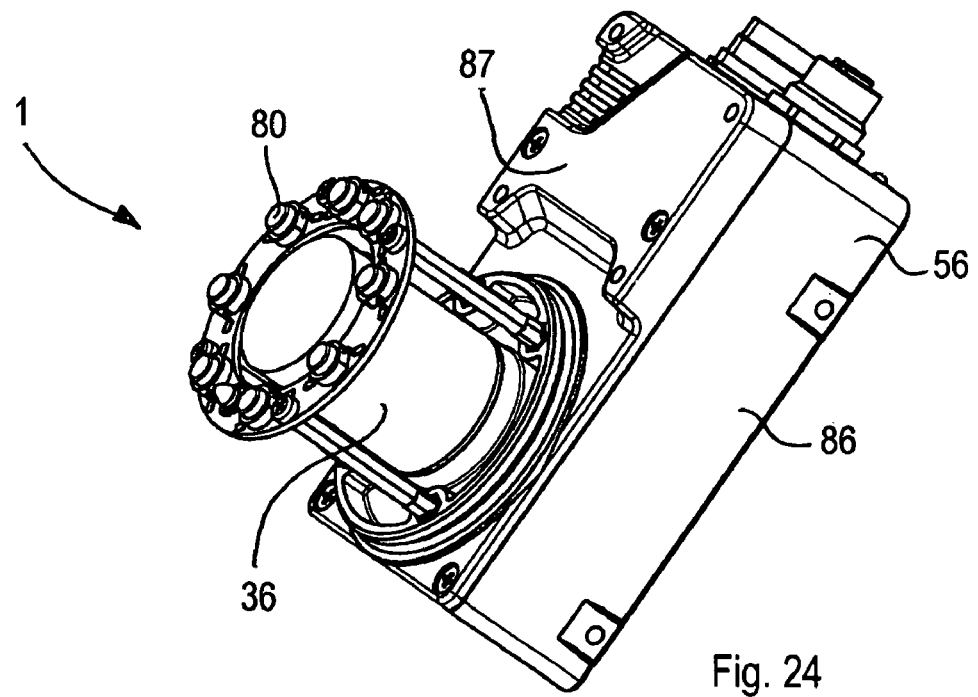
Figure 25:
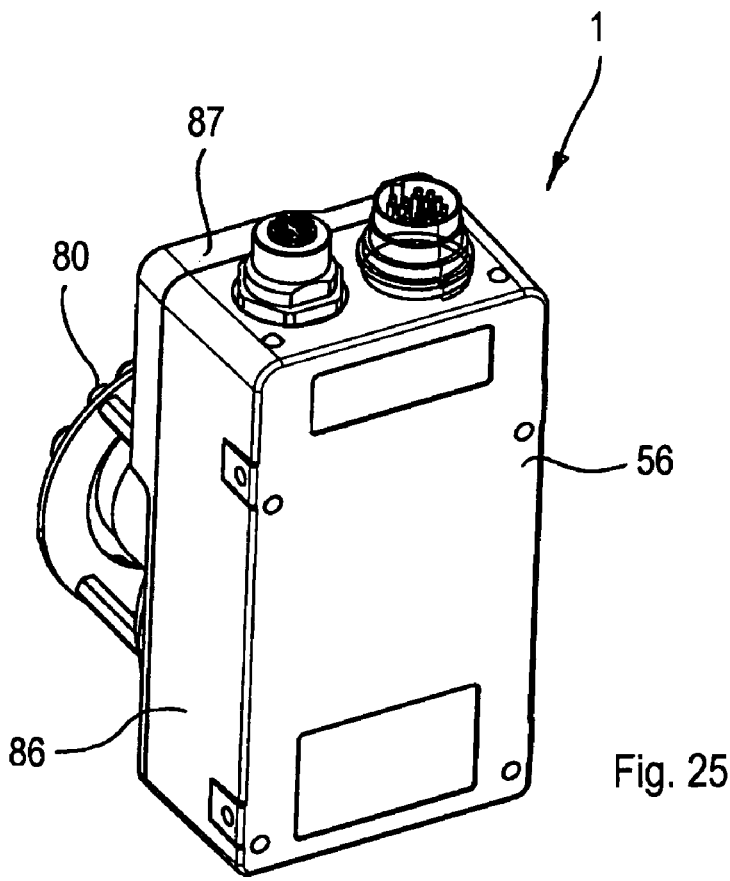
Figure 26:
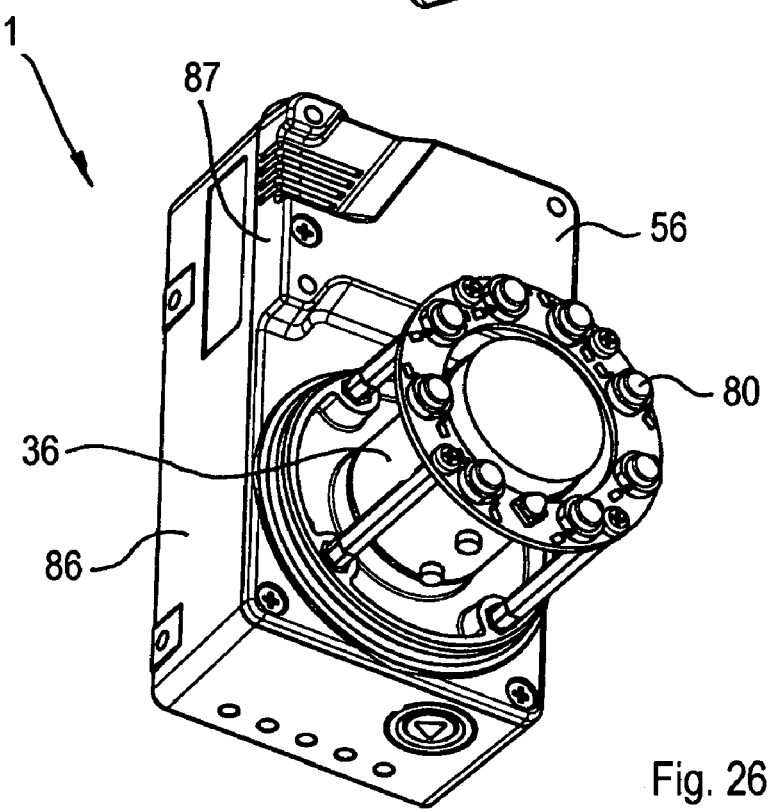
Figure 27:
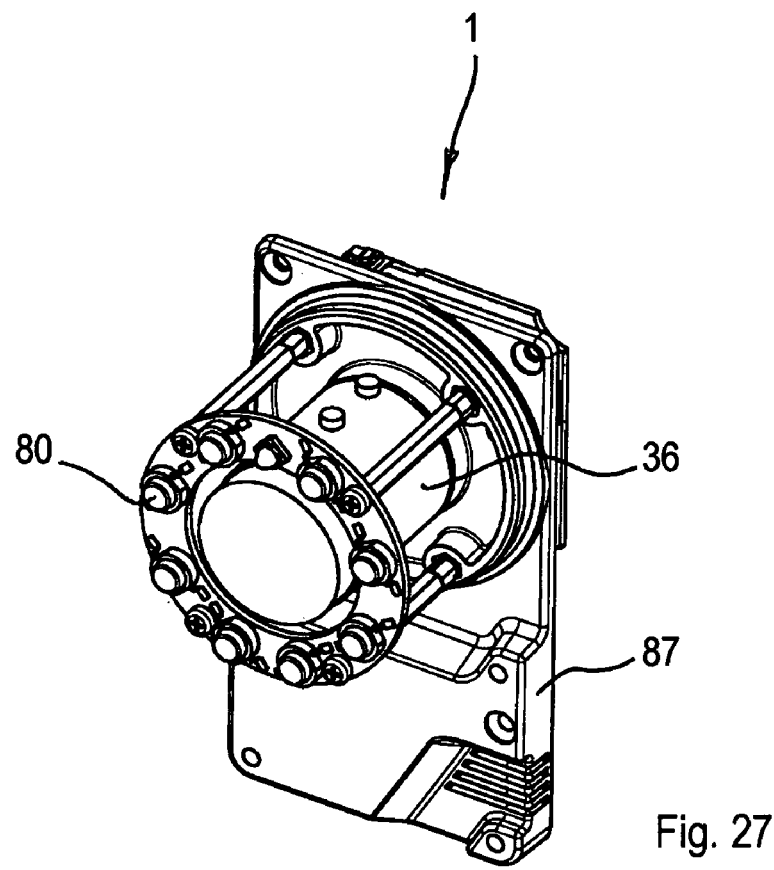
FIGS. 27 to 30 are perspective views of a part of the vision device shown in FIGS. 23 to 26.
Figure 28:
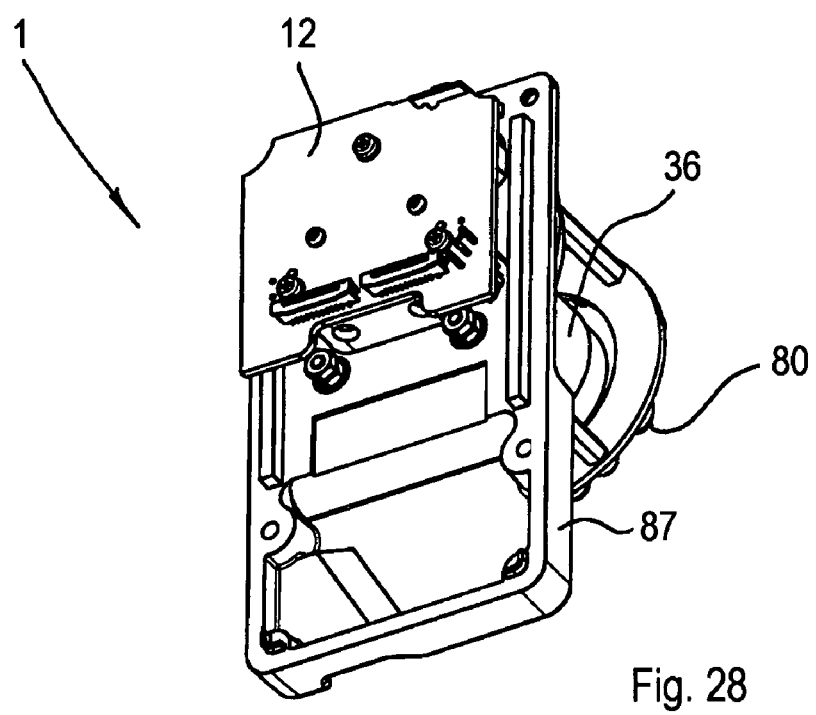
Figure 29:
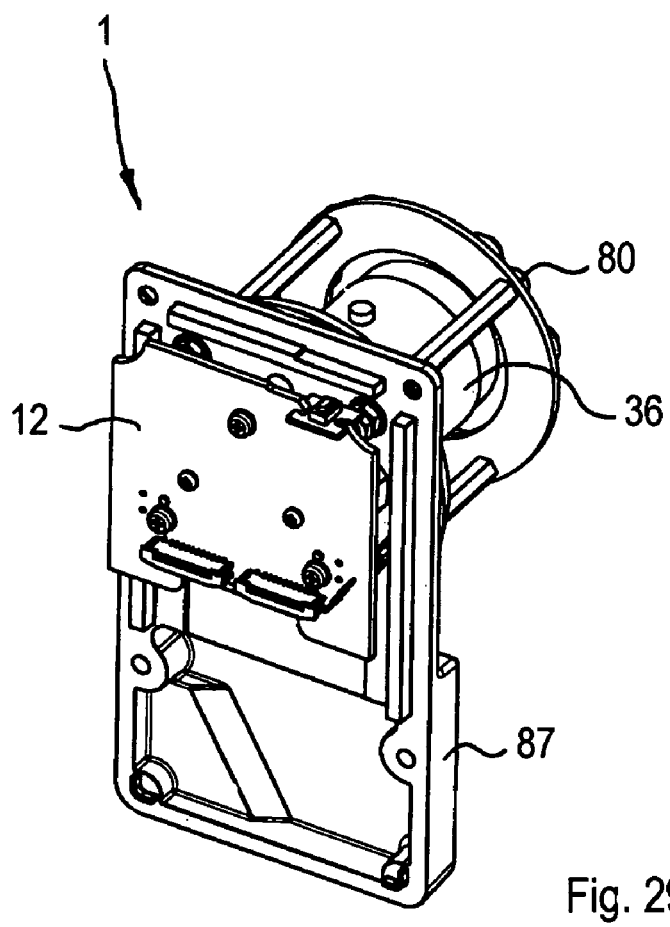
Figure 30:
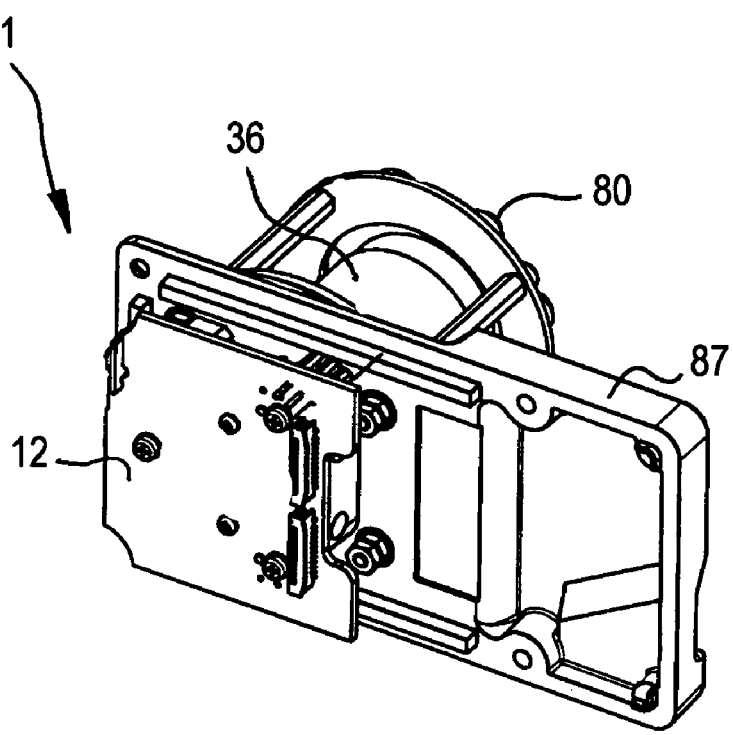
Figure 31:
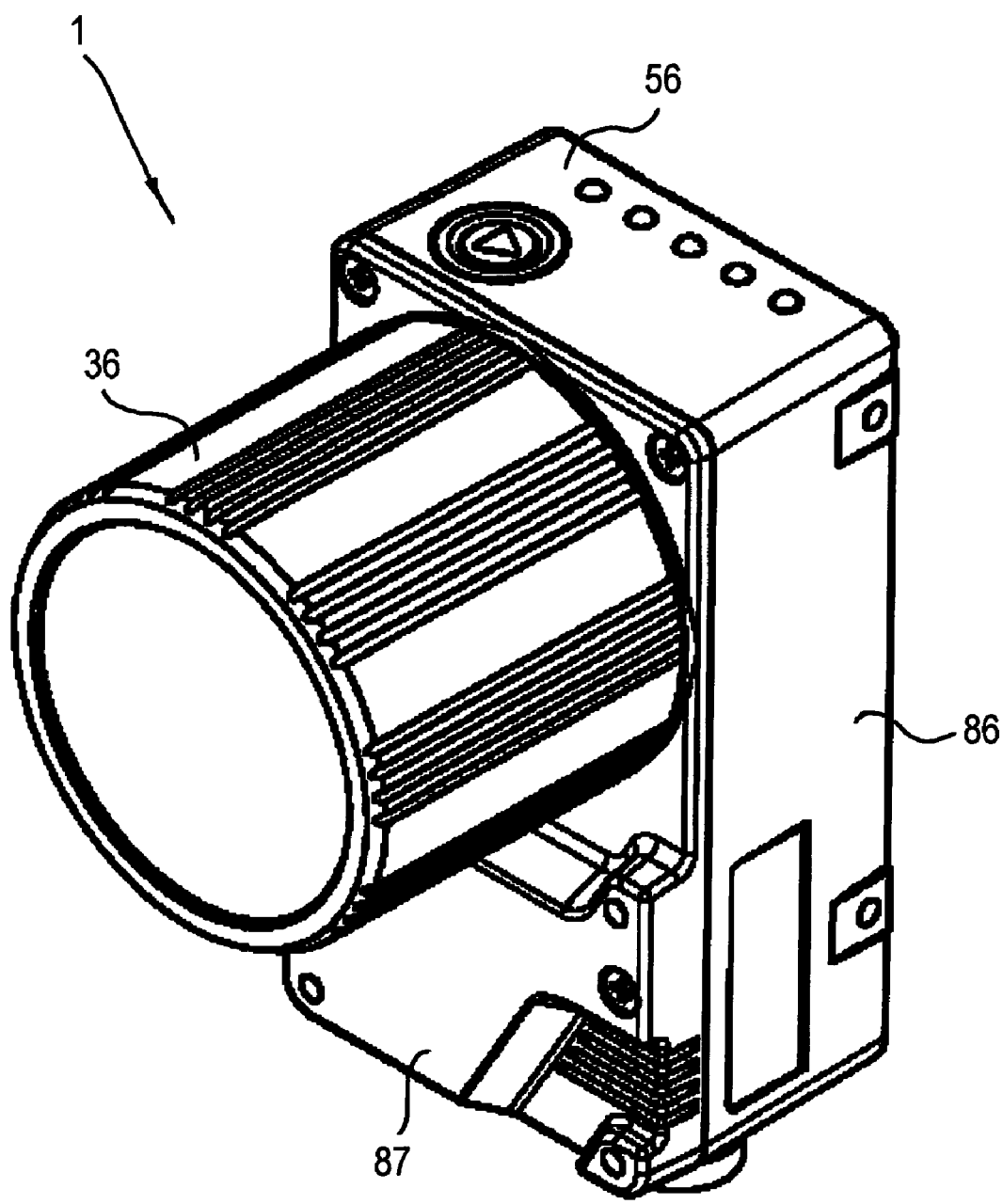
FIG. 31 is a further perspective view of the vision system shown in FIGS. 23 to 26.

As shown in FIG. 22, the light-emitting device 3 may comprise a screen 83 provided with openings or outlines 84 of a preset shape rear-lit by light source 85. The openings or outlines 84 define an emission surface 61f of the light-emitting device 3.

Alternatively, the light-emitting device 3 may comprise a light source and associated optics. In these cases, the position of the "emission surface" of the light-emitting device 3 does not coincide with the real emission surface of the light source, inasmuch as it depends on the properties of the optics associated with the source.

In general, the dimensions of the luminous reference figures depend on the size of the emission surface of the sources of light, on the distance of the reference plane from the objective and on the focal of the objective. The magnification of the luminous reference figure is calculated as a good approximation of the distance/focal ratio.

What is claimed is:

1. A fixed vision system, comprising a sensor for acquiring an image of an object on a detecting plane, said sensor comprising a sensitive surface, a light-emitting device for generating a luminous reference figure on said detecting plane, said light-emitting device comprising an emission surface, and at least an objective through which a luminous radiation and a further luminous radiation pass, said luminous radiation coming from said object and being directed to said sensor and said further luminous radiation coming from said light-emitting device and being directed to said object, wherein said sensor and said light-emitting device are positioned in such a way that, when said detecting plane is focused by said objective on said sensor, said sensitive surface of said sensor is on the image plane generated by said objective or on a respective mirror plane with respect to said image plane and said emission surface of said light-emitting device is on said image plane or on a respective mirror plane with respect to said image plane.

2. System according to claim 1, further comprising a deflecting element arranged for deviating said luminous radiation and/or said further luminous radiation.

3. System according to claim 2, wherein said deflecting element generates at least a mirror plane with respect to said image plane.

4. System according to claim 2, further comprising positioning means arranged for varying a distance defined between said sensitive surface of said sensor and said deflecting element and/or a further distance defined between said emission surface of said light-emitting device and said deflecting element.

5. System according to claim 4, wherein, when said detecting plane is focused by said objective on said sensor, said distance is the same as said further distance.

6. System according to claim 2, wherein said deflecting element comprises a mirror supported by a base body.

7. System according to claim 6, wherein said sensor is fixed to said base body.

8. System according to claim 6, wherein said base body comprises a hole arranged for facing said object in such a way as to enable said luminous radiation to reach said sensor.

9. System according to claim 6, wherein said light-emitting device comprises a light source, said mirror being interposed between said light source and said objective.

10. System according to claim 9, wherein said base body comprises a cavity arranged for receiving said mirror.

11. System according to claim 9, wherein said base body comprises a gap arranged for receiving said light source.

12. System according to claim 9, further comprising a supporting element connectable to said base body and supporting said light source.

13. System according to claim 12, further comprising moving means arranged for moving said supporting element with respect to said base body.

14. System according to claim 9, wherein said light-emitting device further comprises a further light source and a further mirror interposed between said further light source and said objective.

15. System according to claim 14, wherein said base body comprises a cavity arranged for receiving said mirror and a further cavity arranged for receiving said further mirror; or
wherein said base body comprises a gap arranged for receiving said light source and a further gap arranged for receiving said further light source; or
further comprising a supporting element connectable to said base body and supporting said light source and a further supporting element connectable to said base body and supporting said further light source; or
further comprising moving means arranged for moving said supporting element with respect to said base body and further moving means arranged for moving said further supporting element with respect to said base body.

16. System according to claim 2, wherein said deflecting element comprises beam splitting means.

17. System according to claim 16, wherein said beam splitting means deviates at least part of said luminous radiation and does not deviate at least part of said further luminous radiation.

18. System according to claim 17, wherein said sensor has an optical axis arranged transversely to an optical axis of said objective and said emission device comprises a light source having an emitting axis substantially parallel to said optical axis of said objective.

19. System according to claim 1, wherein said sensitive surface of said sensor and said emission surface of said light-emitting device are coplanar.

20. System according to claim 19, wherein said light source is housed in a seat of a package of said sensor.

21. System according to claim 19, wherein said light source is arranged in a substrate of a package of said sensor.

22. System according to claim 19, wherein said sensor comprises a reflecting element coplanar with said sensitive surface of said sensor.

23. System according to claim 22, wherein said light-emitting device comprises a light source arranged for illuminating said reflecting element.

24. System according to claim 1, wherein said light-emitting device comprises a LED provided with a chip shaped in such a way that said luminous reference figure has a specific shape such as to facilitate a visual inspection of focusing.

25. System according to claim 24, wherein said chip comprises at least a bonding arranged in a preset position for giving said luminous reference figure said specific shape.

26. System according to claim 24, wherein said chip comprises at least a metallization line arranged in a preset position for giving said luminous reference figure said specific shape.

27. System according to claim 1, further comprising rotation promoting means arranged for enabling an enclosure of said vision system to rotate with respect to a supporting frame to which said vision system is fixable in such a way that said luminous reference figure provides an indication relating to the field of view of said sensor,
wherein said rotation promoting means is shaped in such a way that said enclosure is rotatable around an optical axis of said objective.

28. System according to claim 1, wherein said objective is an interchangeable objective that can be selected from a plurality of objectives.

29. System according to claim 1, wherein said vision system is a reading system for reading optical information.

30. A method for installing a fixed vision system, comprising the steps of:
providing a fixed vision system, the fixed vision system comprising: a sensor for acquiring an image of an object on a detecting plane, said sensor comprising a sensitive surface, a light-emitting device for generating a luminous reference figure on said detecting plane, said light-emitting device comprising an emission surface, and at least an objective through which a luminous radiation and a further luminous radiation pass, said luminous radiation coming from said object and being directed to said sensor and said further luminous radiation coming from said light-emitting device and being directed to said object, said sensor and said light-emitting device being positioned in such a way that, when said detecting plane is focused by said objective on said sensor, said sensitive surface of said sensor is on the image plane generated by said objective or on a respective mirror plane with respect to said image plane and said emission surface of said light-emitting device is on said image plane or on a respective mirror plane with respect to said image plane;
positioning said vision system at a first distance from said detecting plane;
switching on said light-emitting device; and
adjusting said objective until said luminous reference figure appears to be visually focused on said detecting plane.

31. Method according to claim 30, wherein, during said adjusting, evaluating the focusing of said luminous reference figure with the naked eye is provided.

32. Method according to claim 30, wherein, during said adjusting, maintaining a diaphragm of said objective in a maximum opening configuration is provided.

33. Method according to claim 30, wherein, after said adjusting, moving said detecting plane in such a way that between said vision system and said detecting plane a second distance is provided and checking whether said luminous reference figure appears to be visually focused on said detecting plane at said second distance is provided.

34. Method according to claim 33, wherein said moving comprises moving said detecting plane towards said vision system.

35. Method according to claim 33, wherein, if said luminous reference figure does not appear to be visually focused on said detecting plane at said second distance, acting on a diaphragm of said objective to control the luminosity and the depth of field of said objective is provided until said luminous reference figure appears to be visually focused on said detecting plane at said second distance.

36. Method according to claim 35, wherein said acting comprises partially closing said diaphragm.

37. Method according to claim 33, further comprising further moving said detecting plane in such a way that between said vision system and said detecting plane a third distance is defined, said first distance having an intermediate value between the values of said second distance and said third distance, and checking if said luminous reference figure appears to be visually focused on said detecting plane at said third distance.

38. Method according to claim 37, wherein said moving comprises moving said detecting plane towards said vision system.

39. Method according to claim 37, wherein, if said luminous reference figure does not appear to be visually focused on said detecting plane at said third distance, further acting on said diaphragm of said objective is provided to further control the luminosity and the depth of field of said objective until said luminous reference figure appears to be visually focused on said detecting plane at said third distance.

40. Method according to claim 39, wherein said further acting comprises partially closing said diaphragm.

41. Method according to claim 30, wherein said positioning comprises mounting said vision system above a conveying device that conveys said object.

42. Method according to claim 30, further comprising rotating said vision system with respect to a supporting frame to which said vision system is fixable in such a way that said luminous reference figure provides an indication relating to the field of view of said sensor.

43. Method according to claim 30, wherein said vision system is a reading system for reading optical information.

44. A method for manufacturing a fixed vision system, comprising the steps of:
   assembling a vision system, the vision system including a sensor for acquiring an image of an object on a detecting plane, said sensor comprising a sensitive surface, a light-emitting device for generating a luminous reference figure on said detecting plane, said light-emitting device comprising an emission surface, and at least an objective through which a luminous radiation and a further luminous radiation pass, said luminous radiation coming from said object and being directed to said sensor and said further luminous radiation coming from said light-emitting device and being directed to said object, a deflecting element arranged for deviating said luminous radiation and/or said further luminous radiation,
   positioning said vision system at a preset distance from said detecting plane,
   activating said sensor to detect a sample image,
   adjusting said objective until said sample image is viewed focused by said sensor,
   switching on said light-emitting device, and
   varying the position of said light-emitting device and/or of said deflecting element until a configuration is reached in which said luminous reference figure appears to be visually focused on said detecting plane, in said configuration said sensor and said light-emitting device being positioned in such a way that, when said detecting plane is focused by said objective on said sensor, said sensitive surface of said sensor is on the image plane generated by said objective or on a respective mirror plane with respect to said image plane and said emission surface of said light-emitting device is on said image plane or on a respective mirror plane with respect to said image plane.

45. Method according to claim 44, wherein said varying comprises modifying a distance defined between said sensitive surface of said sensor and said deflecting element and/or further modifying a further distance defined between said emission surface of said light-emitting device and said deflecting element.

46. Method according to claim 45, wherein said varying comprises positioning said sensor, said light-emitting device and said deflecting element in such a way that said distance and said further distance are the same as one another.

47. Method according to claim 44, wherein, during said varying, evaluating the focusing of said luminous reference figure with the naked eye is provided.

48. A method for manufacturing a fixed vision system, comprising a sensor for acquiring an image of an object on a detecting plane, said sensor comprising a sensitive surface, a light-emitting device for generating a luminous reference figure on said detecting plane, said light-emitting device comprising an emission surface, and at least an objective through which a luminous radiation and a further luminous radiation pass, said luminous radiation coming from said object and being directed to said sensor and said further luminous radiation coming from said light-emitting device and being directed to said object, a deflecting element arranged for deflecting said luminous radiation and/or said further luminous radiation, comprising the steps of:
   positioning said vision system at a preset distance from said detecting plane,
   switching on said light-emitting device,
   adjusting said objective until said luminous reference figure appears to be visually focused on said detecting plane,
   activating said sensor to detect a sample image, and
   varying the position of said sensor and/or of said deflecting element until a configuration is reached in which said sample image is viewed focused by said sensor, in said configuration said sensor and said light-emitting device being positioned in such a way that, when said detecting plane is focused by said objective on said sensor, said sensitive surface of said sensor is on the image plane generated by said objective or on a respective mirror plane with respect to said image plane and said emission surface of said light-emitting device is on said image plane or on a respective mirror plane with respect to said image plane.

49. Method according to claim 48, wherein said varying comprises modifying a distance defined between said sensitive surface of said sensor and said deflecting element and/or further modifying a further distance defined between said emission surface of said light-emitting device and said deflecting element.

50. Method according to claim 49, wherein said varying comprises positioning said sensor, said light-emitting device and said deflecting element in such a way that said distance and said further distance are the same as one another.

* * * * *